(12) United States Patent
Wu et al.

(10) Patent No.: US 7,662,547 B2
(45) Date of Patent: Feb. 16, 2010

(54) COMPOSITIONS AND METHODS FOR DETECTING AND TREATING HIV INFECTIONS

(75) Inventors: Yuntao Wu, Manassas, VA (US); Rebecca Alyson Crook Yoder, Fairfax, VA (US); Jeremy Kelly, Arlington, VA (US); Dongyang Yu, Manassas, VA (US)

(73) Assignee: George Mason Intellectual Properties, Inc., Fairfax, VA (US)

( * ) Notice: Subject to any disclaimer, the term of this patent is extended or adjusted under 35 U.S.C. 154(b) by 0 days.

(21) Appl. No.: 11/744,776

(22) Filed: May 4, 2007

(65) Prior Publication Data

US 2008/0064026 A1 Mar. 13, 2008

Related U.S. Application Data

(60) Provisional application No. 60/894,150, filed on Mar. 9, 2007, provisional application No. 60/797,745, filed on May 5, 2006.

(51) Int. Cl.
*C12Q 1/00* (2006.01)

(52) U.S. Cl. ........................................ 435/4; 424/208.1
(58) Field of Classification Search ...................... None
See application file for complete search history.

(56) References Cited

U.S. PATENT DOCUMENTS 6,962,900 B2    11/2005   Zhou et al.

FOREIGN PATENT DOCUMENTS

| EP | 1 542 016 A1 | 6/2005 |
|----|--------------|--------|
| WO | WO 2005/103654 A2 | 11/2005 |

OTHER PUBLICATIONS

International Search Report (PCT/US2007/010750); Date of Mailing: Apr. 24, 2008; 2 pages.

*Primary Examiner*—Stacy B Chen
*Assistant Examiner*—Nicole Kinsey White
(74) *Attorney, Agent, or Firm*—Foley & Lardner LLP; Richard C. Peet; R. Brian McCaslin

(57) ABSTRACT

HIV infection can be detected by measuring phosphorylation levels of the actin-depolymerizing factor (AFD)/cofilin family, and infection can be treated and/or prevented by modulating the HIV co-receptor signaling pathway.

6 Claims, 15 Drawing Sheets

US 7,662,547 B2

COMPOSITIONS AND METHODS FOR DETECTING AND TREATING HIV INFECTIONS

INFORMATION ON RELATED APPLICATIONS

This application claims the priority benefit of U.S. Provisional Application No. 60/797,745 filed on May 5, 2006, and U.S. Provisional Application No. 60/894,150 filed on Mar. 9, 2007, which are hereby incorporated herein by reference.

This invention was made with government support under grant number A1069981 awarded by the National Institutes of Health. The government has certain rights in the invention.

BACKGROUND

HIV infection of susceptible cells, such as CD4+ T-cells, is mediated by the interaction of CD4 and a cell surface chemokine co-receptor with the gp120 envelope protein. The HIV viral particle initially binds via its gp120 envelope protein to the CD4 receptor of the target cell. A conformational change occurs in gp120 that results in its subsequent binding to a chemokine receptor, such as CCR5. See, e.g., Wyatt et al., *Science,* 280:1884-1888 (1998). HIV-1 isolates arising subsequently in the infection bind to the CXCR4 chemokine receptor.

HIV does not immediately replicate in all infected cells, but instead can progress to a state of latent infection, where the HIV is dormant. Upon activation of a latent infected cell, for example by engaging T-cell surface CD3 and CD28, the "dormant" HIV virus can become activated, initiating the process of viral replication. HIV replication results in the production of infectious HIV particles, facilitating the spread of the infection throughout the subject cells.

The pool of latently infected cells in the resting CD4+ T-cell compartment is considered one of the major impediments to HIV eradication. When latently infected, resting T-cells become reactivated, viral particles released during the reactivation process can spread to and infect resting T-cells, as well as activated CD4+ T-cells. This reactivation process can facilitate the continual replenishment of the CD4+ T-cell reservoir, offsetting the benefits of antiviral therapy, such as HAART, and contributing to the persistence of HIV and initiation of new infection cycles. See, e.g., Chun et al., *J. Clin. Invest.* 115:3250-3255, 2005.

Accordingly, methods capable of detecting and treating HIV infection during its latent phase are needed.

SUMMARY

In one aspect, there is provided a method for detecting HIV infection in a patient, comprising measuring the phosphorylation level of cofilin in a sample from the patient. In one embodiment, the phosphorylation level is measured for serine-3. In another embodiment, the measuring is conducted by detecting a phosphorylation-driven conformational change on electron transport.

In another aspect, there is provided a method for treating and/or preventing HIV infection in a patient, comprising: administering to said patient an agent that inhibits HIV trigger receptor signaling; inhibits actin depolymerization; enhances the assembly of actin; stabilizes actin filaments; induces polymerization of monomeric actin; binds to F-actin or cofilin; or inhibits actin and cofilin activity.

In one embodiment, the agent is selected from the group consisting of jasplakinolide, PP2A, PP1, slingshot phosphatases, FR225659, fostriecin, calyculin A, cantharidin, jasplakinolide; phaloidin; chondramides, chondramide A, B, C, and D; (−)-doliculide; dolastatin-11; dolastatin 3-Nor; Majusculamid; dolastatin Hmp; alpha-cyano-3,4-dihydroxy-N-benzylcinnamide (AG490); 1,2,3,4,5,6-; JSI-124; benzylidenemalonitriles ("tyrphostins"); WHI-P154; WHI-P151; pyrrolo[2,3-d]-pyrimidines; benzimisazo[4,5-f] isoquinolinone derivatives; AG1801; WP1034; WP1050; WP1015; WP1-1066; WP1129; WP1130; WP1119; WP1026; WP1127; JSI-124; cucurbitacin I; cucurbitacin A; cucurbitacin B; cucurbitacin D; cucurbitacin E; tetrahydro-cucurbitacin I; PD98059 (2'-amino-3'-methoxyflavone); UO126; SL327; olomoucine; 5-iodotubercidin; arctigenin; 4-bromo or 4-iodo phenylamino benzhydroxamic acid derivatives; N3 alkylated benzimidazole derivatives; FR225659; fostriecin; Calyculin A; okadaic acid; cantharidin; TCM-platinum agents containing demethylcantharidin; genistein; MEK inhibitor, and derivatives thereof.

In another embodiment, the agent inhibits the JAK2 signaling pathway, the tyrosine kinase signaling pathway, the Rac/Pak1/Lmk signaling pathway, or the signal transduction activity of CXCR4. In another embodiment, the agent is a phosphatase inhibitor.

In another aspect, there is provided a method for identifying compounds that inhibit HIV infection, comprising evaluating a compound's ability to alter the phosphorylation state of a protein of the ADF/cofilin family. In one embodiment, the evaluation comprises determining whether the compound can inhibit the dephosphorylation of serine-3 residue of cofilin.

In another aspect, there is provided a composition comprising: (a) an effective amount of a compound selected from the group consisting of: jasplakinolide; phaloidin; chondramides, chondramide A, B, C, and D; (−)-doliculide; dolastatin-11; dolastatin 3-Nor; Majusculamid; dolastatin Hmp; alpha-cyano-3,4-dihydroxy-N-benzylcinnamide (AG490); 1,2,3,4,5,6-; JSI-124; benzylidenemalonitriles ("tyrphostins"); WHI-P154; WHI-P151; pyrrolo[2,3-d]-pyrimidines; benzimisazo[4,5-f]isoquinolinone derivatives; AG1801; WP1034; WP1050; WP1015; WP1-1066; WP1129; WP1130; WP1119; WP1026; WP1127; JSI-124; cucurbitacin I; cucurbitacin A; cucurbitacin B; cucurbitacin D; cucurbitacin E; tetrahydro-cucurbitacin I; PD98059 (2'-amino-3'-methoxyflavone); UO126; SL327; olomoucine; 5-iodotubercidin; arctigenin; 4-bromo or 4-iodo phenylamino benzhydroxamic acid derivatives; N3 alkylated benzimidazole derivatives; FR225659; fostriecin; Calyculin A; okadaic acid; cantharidin; TCM-platinum agents containing demethylcantharidin; genistein; and derivatives thereof; (b) an effective amount of an anti-retroviral agent; and (c) a pharmaceutically acceptable excipient.

BRIEF DESCRIPTION OF THE DRAWINGS

FIG. 1A shows actin polymerization by SDF1. FIG. 1B show: actin depolymerization by gp120. FIG. 1C shows confocal microscopy of resting T cells treated with SDF-1 (50 ng/ml), HIV-1 (ng of 24) or gp120 (50 nM), respectively and stained with FITC-phalloidin. FIG. 1D shows HIV-1 mediated cortical actin depolymerization, The bright resting T cell (untreated control) and the dime cells (HIV-1 treated) were selected and compared. The relative intensity of F-actin staining was measured along arrows (n=1000 measurements per line) and plotted at the bottom. FIG. 1E shows cytosolic (non-cortical) F-actin staining between HIV-1 treated and untreated cells detected no difference, The intensity of cytosolic F-actin staining in randomly selected cells (equal number of infected versus uninfected) was measured along the folded lines (n=1,000 measurements per line) and shown as the mean ±SD on the right (P>0.117, n=20,000).

FIG. 2A shows actin depolymerization by anti-CD4/CXCR4 antibodies conjugated to BD IMag particles. FIG. 2B shows actin depolymerization by anti-CXCR4 but not anti-CD4 BD IMag particles. FIG. 2C shows HIV-1 mediated actin depolymerization was dependent on P.T-sensitive signaling. Cells were not treated (left panel) or treated with P.T right panel). followed by HIV-1 infection (ng of p24 per $10^6$ cells) a d staining with FITC-phallodin for F-actin.

FIG. 3A graphically shows the effects of Jas on HIV-1 latent infection of resting T cell FIG. 3B shows the effects of Jas on viral entry. FIG. 3C graphically shows the effects of Jas on HIV-1 infection of pre-activated r cells. FIG. 3D graphically shows the effects of Jas on HIV-1 infection of transformed cells. FIG. 3E graphically shows the effects of Jas on HIV-1 infection of resting T cells pre-stimulated with anti-CD4/CXCR4 bead (2 beads/cell).

FIG. 4A shows dose-dependent actin depolymerization by Lat-A. FIG. 4B shows time-dependent actin depolymerization by Lat-A, FIG. 4C graphically shows enhancement of HIV-1 latent infection by Lat-A, FIG. 4D graphically shows dose-dependent enhancement of viral replication by Lat-A.

FIG. 5B shows activation of cofilin by gp120, FIG. 5C shows activation of cofilin by anti-CD4/CXCR4 bead (two beads/cell). FIG. 5D shows activation of cofilin by gp120promotes its association with actin cytoskeleton, F-actin fractions were prepared from gp120treated resting T cells and immunoblotted for actin (upper band) and cofilin (lower band), FIG. 5E shows P,T-sensitive activation of cofilin by HIV-1, Cells were not treated (left panel) or treated (right panel) with P.T then infected and analyzed as in FIG. 5A. FIG. 5F shows constitutive activation of cofilin in transformed cell lines, P-cofilin (upper band) and active cofilin (lower band) was separated by NEPHGE-western blotting and the relative ratio of P-cofilin to active cofilin was indicated at the bottom, Resting CD4 T cells were used as control at the right end. FIG. 5G shows F-actin staining of CEM-SS cells infected with HIV-1. FIG. 5H shows cofilin activation induced by PHA plus IL-2 and HIV-1 treatment of resting CD4 T cells.

FIG. 6A shows cofilin specific S3 peptide activates cofilin through competitive inhibition of cofilin phosphorylation by LIMK1. FIG. 6B shows dosage dependent enhancement of viral replication by S3. FIG. 6C shows viral replication course in cells similarly treated and infected as in FIG. 6B. FIG. 6D shows that staurosporine induces cofilin activation in resting T cells. Cells were treated with Staurosporine and immunoblotted for P-cofilin and total cofilin. FIG. 6E shows that staurosporine induces actin depolymerization in resting T cell. FIG. 6F shows staurosporine induces cofilin activation by direct inhibition of LIMK1 FIG. 6G show enhancement of viral replication by Staurosporine, FIG. 6H shows a model of gp120-CXCR4 signaling in mediating cofilin activation.

FIG. 11A is an immunoblot using P-cofilin (Ser3) or cofilin on resting CD4 T cells from five HIV patients on HAART therapy and five healthy donors, FIG. 11B shows the relative ratio of P-cofilin to cofilin, HIV-1 positive donors have statistically significant lower levels of P-cofilin/cofilin (p=0.001)suggesting higher levels of active cofilin, FIG. 11C shows the absolute ratios of P-cofilin to active cofilin in three health donors confirmed by NEPHEGE western blotting using an anti-cofilin antibody, FIG. 11D shows the absolute ratios of P-cofilin to active cofilin in three HIV infected donors confirmed by NEPHEGE western blotting using an anti-cofilin antibody.

DETAILED DESCRIPTION

Figure 1:
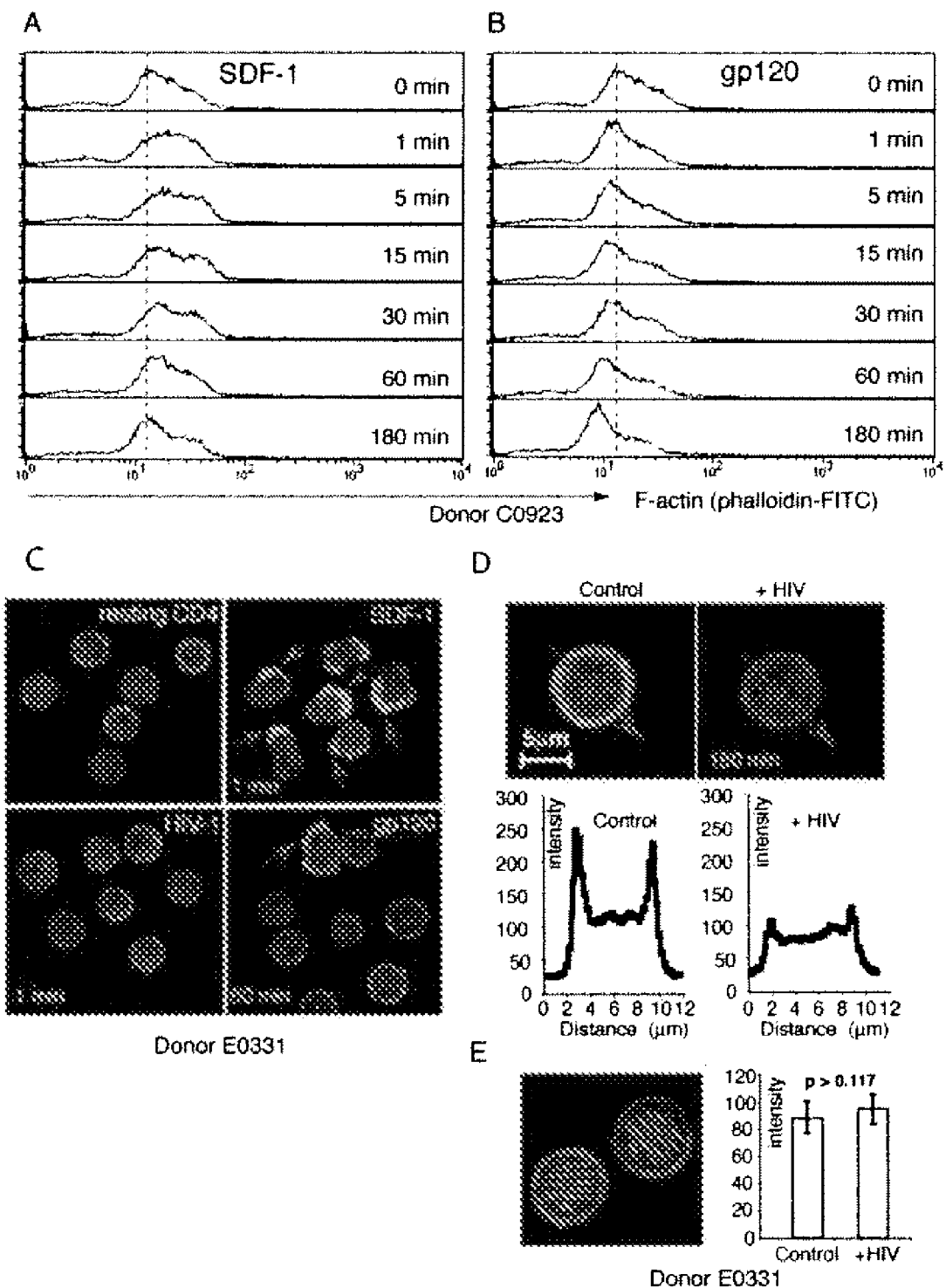
FIG. 1: HIV-1 gp120 mediates depolymerization of cortical actin in resting CD4 T cells.

HIV infection can be detected by measuring signal transduction cascade events, such as evaluating phosphorylation levels of actin-depolymerizing factor (ADF)/cofilin family members. For example, HIV infection of resting T-cells results in cofilin activation by dephosphorylation at serine-3. Thus, monitoring the phosphorylation state of cofilin can be used to detect HIV in patient samples and to monitor disease progression. Moreover, inhibitors of phosphorylation of actin-depolymerizing factor (ADF)/cofilin family members can be used to treat HIV infection.

All technical terms in this description are commonly used in biochemistry, molecular biology and immunology, respectively, and can be understood by those skilled in the field of this invention. Those technical terms can be found in: MOLECULAR CLONING: A LABORATORY MANUAL, 3rd ed., vol. 1-3, ed. Sambrook and Russel, Cold Spring Harbor Laboratory Press, Cold Spring Harbor, N.Y., 2001; CURRENT PROTOCOLS IN MOLECULAR BIOLOGY, ed. Ausubel et al., Greene Publishing Associates and Wiley-Interscience, New York, 1988 (with periodic updates); SHORT PROTOCOLS IN MOLECULAR BIOLOGY: A COMPENDIUM OF METHODS FROM CURRENT PROTOCOLS IN MOLECULAR BIOLOGY, $5^{th}$ ed., vol. 1-2, ed. Ausubel et al., John Wiley & Sons, Inc., 2002; GENOME ANALYSIS: A LABORATORY MANUAL, vol. 1-2, ed. Green et al., Cold Spring Harbor Laboratory Press, Cold Spring Harbor, N.Y., 1997; CELLULAR AND MOLECULAR IMMUNOLOGY, 4th ed. Abbas et al., W B Saunders, 1994.

DEFINITIONS

Cofilin refers to a protein sequence that reversibly controls actin polymerization and depolymerization in a pH-sensitive manner. Cofilin has the ability to bind G- and F-actin in a 1:1 ratio of cofilin to actin. As used herein, cofilin refers to the functionally active cofilin molecule which is not phosphorylated and which is capable of perturbing the cell cytoskeleton. Exemplary cofilin polynucleotide and polypeptide sequences are set forth in SEQ ID NO: 1 and 2, respectively.

An "effective amount" is the amount of an agent (or combination of agents) that is successful in achieving the desired purpose, for example, treating HIV infection; inhibiting replication of HIV in latently infected cells; inhibiting HIV infection; etc. The specific dose level and frequency of dosage may vary, and can depend upon a variety of factors, including the activity of the specific active agents, their metabolic stability and length of action, rate of excretion, mode and time of administration, and the age, body weight, general health, gender, diet, severity of the disease, viral load, clinical course of HIV infection, CD4+ T-cell count, of the particular subject who is undergoing therapy. The combination of agents can be synergistic, i.e., where the joint action of the agents is such that the combined effect is greater than the algebraic sum of their individual effects.

The "HIV co-receptor pathway" includes the HIV co-receptors (e.g., CXCR4, CCR5, etc) that are used for virus entry into cells, and downstream members of its signaling pathway. Such members include but are not limited to, for example, G-proteins; JAK1, JAK2, JAK3; tyrosine kinases, such as MEK1 and/or MEK2; Rac1/PAK1/LIMK; cofilin; phosphatases, such as PP1, PP2A, hSSH, and/or Chronophin; etc. A member of co-receptor signaling pathway can also be described as an effector of co-receptor stimulation, i.e., that is modulated upon co-receptor stimulation by HIV envelope protein.

"Preventing" HIV infection indicates that a subject's susceptibility to HIV infection upon exposure to the virus is reduced or diminished as a result of the administration of an agent of the present invention. Any amount of reduced susceptibility (i.e., resistance) is useful, for example, about 2-fold less, about 5-fold less, about 10-fold less, and any other such improvements can be regarded as preventative.

The term "treat" is used conventionally to mean, for example, the management or care of a subject for the purpose of combating, alleviating, reducing, relieving, improving, eliminating, etc., one or more signs or symptoms associated with HIV infection. Treatment includes delaying the progression of HIV and its associated symptoms, thereby extending the life expectancy of an infected subject, and/or delaying or reducing the onset of symptoms associated with HIV infection. Treating can involve inhibiting, reducing, diminishing, blocking, etc., HIV replication, especially in latently infected cells; reducing, decreasing, diminishing, etc. HIV viral load in infected subjects; preventing, inhibiting, blocking establishment of HIV latent infection; as well as modulating other events in the life cycle of the HIV virus.

I. Detecting HIV Infection

The actin filament network is involved in a diverse number of cellular processes, including control of cell polarization, orientation, intracellular trafficking, membrane fusion, and motility. Proteins of the actin-depolymerizing factor (ADF)/cofilin (AC) family dynamically regulate these cytoskeletal arrangements by increasing the turnover of actin. Cofilin activity is regulated by phosphorylation at serine 3 which prevents its association with actin, whereas dephosphorylation by phosphatases such as PP1, PP2A or Slingshot (SSH) activates cofilin and promotes its association with actin and increase actin dynamics.

In eukaryotic cells, the most important physiological function of cofilin is to sever and depolymerize actin filaments promoting actin dynamics. In vitro, ADF/cofilin directly binds to both G- and F-actin and depolymerizes F-actin by changing the twist of actin filaments or stabilizing a preexisting tilted conformation of actin subunits. In vivo, cofilin has been shown to be the primary regulator of cortical actin in yeast, and is among the minimal set of proteins in the actin tail required for the motility of the intracellular pathogen *Listeria*.

In the human immune system, cofilin has been implicated in sustaining T cell activation. In particular, co-stimulation activates cofilin and promotes its direct association with F-actin to increase actin dynamics. Cofilin activity is regulated by phosphorylation at serine-3, which prevents its association with actin, whereas dephosphorylation by phosphatases activates cofilin. Because HIV infection of resting T cells in vitro results in cofilin activation, the phosphorylation state of cofilin serine-3 may be used as a diagnostic marker for HIV infection.

A variety of methods for analyzing protein phosphorylation states are known in the art. For example, proteins can be isolated for western analysis using a rabbit anti-cofilin antibody and a rabbit anti-phospho-cofilin (ser3) antibody. In another example, a phosphorylation state can be determined by measuring a phosphorylation-driven conformational change on electron transport. Work by others has demonstrated that helix unfolding impacts the rate of electron transport in a dichromomorphic peptide model, resulting in an order of magnitude difference in electron transport. Fox et al., *J. Am. Chem. Soc.*, 119:5277-5285 (1997). A 10-fold difference, for example, in electron transport resulting from the addition of the phosphate group onto the surface of the peptide is likely attributable to a conformational shift within the secondary structure of the peptide. Additionally, phosphorylation may increase the space between atoms within a peptide, and as a result the entire length of a peptide may increase. Cofilin phosphorylation also can be measured by mass spectrometry.

II. Treating and/or Preventing HIV

HIV infection can be treated and/or prevented by administering an agent that modulates the HIV co-receptor signaling pathway stimulated by HIV envelope protein gp120. In some embodiments, such an agent can inhibit HIV trigger receptor signaling, actin depolymerization; enhance the assembly of actin; stabilize actin filaments; induce polymerization of monomeric actin; bind to F-actin or cofilin; and/or inhibit actin and cofilin activity.

The effect of a compound on the cell's cytoskeleton can be determined routinely accordingly to any suitable method, including methods commonly known in the art. See, for example, Bubb et al., *J. Biol. Chem.*, 276(7):5163-5170 (2000).

Illustrative agents that stabilize or inhibit depolymerization of the actin cytoskeleton include but are not limited to jasplakinolide, phaloidin, chondramides, such as chondramide A, B, C, and D (e.g., Sasse et al., *Journal of the National Cancer Institute*, 90(20), 1559-1563, 1998); (−)-doliculide (e.g., Bai et al., *J. Biol. Chem.*, 277 (35), 32165-32171, 2002; Ishiwata et al., *J. Org. Chem.* 59, 4710-4711, 1994; Ishiwata et al., *J. Org. Chem.* 59, 4712-4713, 1994); dolastatin-11 and derivatives thereof, such as 3-Nor, Majusculamide, and Hmp derivatives (e.g., Ali et al., *Bioorgan. Med. Chem.,* 13: 3138-4152, 2005). Useful agents include those which have the same or similar activity to jasplakinolide; inhibit actin depolymerization; enhance the assembly of purified actin; stabilize actin filaments in vitro; induce polymerization of monomeric actin; and/or bind to F-actin.

Cofilin inhibitors include but are not limited to agents that increase the amount of phosphorylated cofilin (inactive); and/or decrease the amount of functionally active cofilin (i.e., not phosphorylated). Such agents, for example, promote phosphorylation of cofilin; provide peptide derivatives of cofilin which inhibit cofilin phosphatases, such as hSSH inhibitors. Agents which activate pathways such as Rac1/PAK1,2, Rho/Rock that lead to activation of LIMK and actin polymerization can inhibit cofilin activity (increase phosphorylation) and inhibit HIV infection of resting CD4 T cells.

JAK/Stat Signaling Pathway inhibitors can be used to treat and/or prevent HIV infection. Illustrative inhibitors include but are not limited to JAK1, JAK2, STATS (e.g., STAT1, STAT3 (T-cell sub-type), STAT4, and STAT5), hTid1 (member of the DnaJ family of chaperones), Hsp70, TAT inhibitor oligonucleotides (U.S. Pat. No. 7,002,003); JSI-124, cucurbitacin I, cucurbitacin A, cucurbitacin B, cucurbitacin D, cucurbitacin E, and tetrahydro-cucurbitacin I, and derivatives thereof (e.g., see, U.S. Pub. Appl. No. 2004/0138189), Jalpha-cyano-3,4-dihydroxy-N-benzylcinnamide (AG490); 1,2,3,4,5,6-hexabromocyclohexane (Sandberg et al., *J Med Chem.* 2005 Apr. 7; 48(7):2526-33); JSI-124 (Nefedova et al., *Cancer Res.* 2005 Oct. 15; 65(2):9525-35); benzylidenemalonitriles ("tyrphostins") (see, also, U.S. Pat. No. 6,433,018; U.S. Pub. Pat. App. No. 2003/0013748); quinazolines (WHI-P154, and WHI-P151); pyrrolo[2,3-d]-pyrimidines; benzimisazo[4,5-f]isoquinolinone derivatives (e.g., U.S. Pat. No. 6,852,727); AG1801, WP1034, WP1050, WP1015, WP1-1066, WP1129, WP1130, WP1119, WP1026, WP1127, and derivatives thereof, as well as other compounds and derivatives thereof (such as WP1002-WP1127), e.g., disclosed in U.S. Patent Application Publication No. 2005/0277680.

A tyrosine kinase inhibitor can be used to treat and/or prevent HIV infection. Exemplary inhibitors include but are not limited to MEK inhibitors, such as PD98059 (2'-amino-3'-methoxyflavone), UO126, SL327, olomoucine, 5-iodotubercidin, arctigenin, etc. Other examples of MEK inhibitors are disclosed in U.S. Pub. App. Nos. 20060052608 (e.g. 4-bromo or 4-iodo phenylamino benzhydroxamic acid derivatives); 20050267012; 20050256123; 20050143438 (N3 alkylated benzimidazole derivatives); 20050130976 (bicyclic inhibitors); 20050059710 (diphenylaminoketone); 20050004186; 20040087583 (amino-thio-acrylonitriles); 20030092748 (benzenesulfonamide derivatives); 20030045521 (sulfohydroxaminic acids and sulfohydroxamates). EGF receptor and pp60 v-src kinase inhibitors also can be utilized, including, e.g., genistein (4',5,7-trihydroxyisoflavone) and derivatives thereof (e.g., U.S. Pub. Pat. App. 20030212009), e.g., which have activity on serine and threonine-dependent protein kinases. Genistein also inhibits kv1.3 potassium channels on T-cells (See Teisseyre et al., *Membr Biol.* 2005 May; 205(2):71-9), and has estrogenic activity.

Phosphatase inhibitors also can be used to treat and/or prevent HIV infection. Phosphatase inhibitors, such as PP1 and PP2A, can inhibit cofilin by dephosphorylation of cofilin. They also may inhibit cofilin activation through acting on LMK1,2, thereby increasing phospho-LIMK1,2. Other phosphatases examples include, but are not limited to, FR225659 (inhibits catalytic subunits of PP1 and PP2A; Hatori et al. *J. Antibiot.* (Tokyo), 2004 July; 57(7):456-461); fostriecin (e.g., Lewy et al., *Curr Med Chem.* 2002 November; 9(22):2005-32); Calyculin A (e.g., Ishihara et al., *Biochem Biophys Res Commun.* 1989 Mar. 31; 159(3):871-7); okadaic acid; cantharidin; TCM-platinum anticancer agents containing demethylcantharidin (e.g., To et al., *Bioorg Med Chem.* 2004 Sep. 1; 12(17):4565-73); and derivatives thereof. Phosphatase assays to determine inhibitor activity can be carried out routinely, e.g., as described in Soosairajah et al. *EMBO J.* 9:24(3):473-86 (2005).

Rac signaling pathway inhibitors also can be used to treat and/or prevent HIV infection. Examples include, but are not limited to, Rac GTPase inhibitors such as NSC-23766 (Gao et al. *PNAS USA,* 101: 7618-7623, 2004), SCH-51344 (Walsh et al. *Oncogene,* 5, 2553-2560, 1997); Rho Kinase inhibitors such as HA 1077 (Shirotani et al. *J. Pharmacol. Exp. Ther.* 259, page 738, 1991), N-(4-Pyridyl)-N'-(2,4,6-trichlorophenyl)urea (Takami et al. *Bioorg. Med. Chem.* 12, page: 2115, 2004), Y-27632 (Maekawa, et al., *Science,* 285, page: 895, 1999); and PAK inhibitors such as K562a and its derivatives such as CEP-1347 (Nheu et al. *Cancer J.,* 8, pages: 328-36, 2002), and WR-PAK18 (Nheu et al. *Cell Cycle,* 3, pages: 71-74, 2004). Additionally, genetic approaches also can be used to inhibit the Rac Signal Pathway. For example, a dominant-negative Rac1 can directly inhibit Rac1 (Qiu et al., *Nature,* 374, pages: 457-459, 1995) and introducing p57/Kip2 can inhibit LIMK (Yokoo et al. *J. Biol. Chem.* 278, pages: 52919-52923, 2003).

Table 1 provides a list of inhibitors and there putative sites of action.

TABLE 1

| Inhibitor | Site of Action |
| --- | --- |
| PD98059 | Map Kinase Kinase (MEK) |
| SB203580 | p38 Map Kinase |
| U0126 | MEK1 and MEK2 |
| Thapsigargin ($C_{24}H_{35}N_7$ 3HCl 0.5 $H_2O$) | induces release of Ca Rac1 |
| Dantrolene | blocks Ca release from the sarcoplasmic reticulum |
| SB202190 | inhibitor of p38 MapKinase |
| JNK Inhibitor II | inhibits c-Jun-N-terminal kinase |
| tyrphostin A9 | tyrosine kinase inhibitor, PDGF receptor and Pyk2 |
| C3-exoenzyme | Rho inhibitor |
| Y-27632 | ROCK inhibitor |
| PTP Inhibitor 1 | inhibits SHP-1 |
| SB202190 | p38 MAP Kinase |
| SB202474 | negative control for SB202190 |
| Okadaic Acid | PP1alpha, PP2A |
| Staurosporine | General Protein Kinase Inhibitor (PKC) |
| Calyculin A | PP1 alpha, PP2A |
| FK506 | calcineurin/PP2B |
| B581 | Ras |
| LY-294002 | PI3Kinase |
| Wortmannin | PI3Kinase |
| Vinblastine | Microtubule Formation |
| Colchicine | Microtubule Formation |
| Nocodazole | Microtubule Formation |
| Taxol | Microtubule Formation |
| Genistein | Protein tyrosine kinase |
| PP2 | Src family of tyrosine kinase |
| PP3 | Negative control for PP2 Inhibitor |
| AG1478 | EGFR kinase inhibitor |
| AG1296 | PDGF receptor kinase |
| JAK2 Inhibitor II | JAK2 |
| AG490 | EGFR kinase inhibitor/JAK2 |
| 4-hydroxyphenacyl Br | protein tyrosine phosphatase (PTP) |
| Cytochalasin B | actin |
| Cytochalasin D | actin |
| Latrunculin A | actin |
| Swinholide A | actin |
| Misakinolide A | actin |

TABLE 1-continued

| Inhibitor | Site of Action |
| --- | --- |
| Tolytoxin | actin |
| Mycalolide B | actin |
| Halichondramide | actin |
| Aplyronine A | actin |
| Pectenotoxin 2 | actin |
| Phalloidin | actin |
| Jasplakinolide | actin |
| Dolastatin 11 | actin |
| Hectochlorin | actin |
| Doliculide | Actin |
| Migrastatin | cell migration |
| Motuporamine C | cell migration |

Administration of Therapeutic Agents

Therapeutic agents can be administered in any form by any effective route, including but not limited to oral, parenteral, enteral, intraperitoneal, topical, transdermal (e.g., using any standard patch), ophthalmic, nasally, local, non-oral, such as aerosol, spray, inhalation, percutaneous (epidermal), subcutaneous, intravenous, intramuscular, buccal, sublingual, rectal, vaginal, intra-arterial, mucosal, and intrathecal. The agent can be administered alone, or in combination with any ingredient(s), active or inactive.

Any subject can be administered a therapeutic agent, including subjects who have been exposed to HIV, but have not yet developed HIV infection, as well as subjects who have progressed to one or more of the clinical symptoms of HIV infection (e.g., AIDS). In addition to treating and/or preventing HIV infection in humans, agents can be used to treat other organisms (e.g., non-human primates, cats, etc.) infected with HIV, or HIV-related viruses, such as SIV, SHIV, or FIV. Thus, subjects who can be treated include, e.g., mammals, humans, monkeys, apes, chimpanzees, gorillas, cats, dogs, mice, rats, etc.

A therapeutic agent can be used to treat and/or prevent infection caused by any HIV virus type, including, but is no limited to, HIV-1 (e.g., clades A, B, C, D, and G, R5 and R5X4 viruses, etc.), HIV-2 (e.g., R5 and R5X4 viruses, etc.), simian immunodeficiency virus (SIV), simian/human immunodeficiency virus (SHIV), feline immunodeficiency virus (FIV), bovine immunodeficiency virus (BIV) (Wright et al., *Vet. Res. Commun.*, 26:239-50, 2002), HTLV-1, HTLV-2, etc.

In one example, HIV infection can be treated and/or prevented by administering an effective amount of an agent selected from the group consisting of jasplakinolide; phaloidin; chondramides, chondramide A, B, C, and D; (–)-doliculide; dolastatin-11; dolastatin 3-Nor; Majusculamid; dolastatin Hmp; alpha-cyano-3,4-dihydroxy-N-benzylcinnamide (AG490); 1,2,3,4,5,6-; JSI-124; benzylidenemalonitriles ("tyrphostins"); WHI-P154; WHI-P151; pyrrolo[2,3-d]-pyrimidines; benzimisazo[4,5-f]isoquinolinone derivatives; AG1801; WP1034; WP1050; WP1015; WP1-1066; WP1129; WP1130; WP1119; WP1026; WP1127; JSI-124; cucurbitacin I; cucurbitacin A; cucurbitacin B; cucurbitacin D; cucurbitacin E; tetrahydro-cucurbitacin I; PD98059 (2'-amino-3'-methoxyflavone); UO126; SL327; olomoucine; 5-iodotubercidin; arctigenin; 4-bromo or 4-iodo phenylamino benzhydroxamic acid derivatives; N3 alkylated benzimidazole derivatives; FR225659; fostriecin; Calyculin A; okadaic acid; cantharidin; and TCM-platinum agents containing demethylcantharidin.

Pharmaceutical Combinations

Therapeutic agents also can be combined with other agents, especially agents which are utilized to treat HIV. Examples of drugs which can be combined with an agent of the present invention include but are not limited to protease inhibitors, reverse transcriptase inhibitors (includes nucleoside/nucleotide drugs and non-nucleoside inhibitors), integrase inhibitors, attachment inhibitors, chemokine receptor inhibitors, RNAase H inhibitors, entry inhibitors; assembly and budding inhibitors; etc. Classes of HIV drugs include but are not limited to attachment inhibitors (TNX-355, BMS-488043), CCR5 coreceptor antagonists (SCH-D, UK-427857, GW 873140) and a maturation inhibitor (PA-457). See, McNicholl and McNicholl, *Curr Pharm Des.* 12(9):1091-103.

Examples of HIV drugs which can be combined with agents include, but are not limited to, abacavir, saquinavir, ritonavir, indinavir, nelfinavir, amprenavir, lopinavir, atazanavir, fosamprenavir, tipranavir, enfuvirtide, tenofovir, entricitabine, AZT, ddI, ddC, ddT, 3TC, d4T, ZDV, nevirapine, delavirdine, etc. In addition, drugs also include, e.g., BMS-48804; UK427,857; TAK-652; GW 871340; CMPD 167; AMD3100; Amdoxovir; TMC278; BILR 355BS; Capravirine; KMMP05; L-870810; FZ41; Tipranavir; TMC114; UIC-020301; GW640385; AG-001859; PA-457; etc. Agents of the present invention also can be combined with vaccines and other preventative measures. See, e.g., U.S. Pat. No. 6,962,900

Suitable excipients for use in a pharmaceutical composition include, but are not limited to, a lubricant, glidant, diluent, binder, disintegrant, carrier, colorant, or coating material. Examples of pharmaceutically acceptable excipients include, but are not limited to, lactose, sugar, corn starch, modified corn starch, mannitol, sorbitol, silicon dioxide, and microcrystalline cellulose.

Anti-retroviral agents attempt to treat HIV infections by inhibiting replication of the HIV virus by blocking the reverse transcriptase or by blocking the HIV protease. Three categories of anti-retroviral agents in clinical use are nucleoside analogs (such as AZT), protease inhibitors (such as nelfinavir), and the recently introduced non-nucleoside reverse transcriptase inhibitors (NNI) such as nevirapine. Any anti-retroviral agent may be used in a pharmaceutical composition.

Vaccines

HIV vaccines for treating and/or preventing HIV infection can comprise a gp120 polypeptide in which the chemokine signaling domain is deleted or mutated to eliminate or reduce its ability to stimulate the cell signaling activity of its cognate chemokine receptor. Such a gp120 polypeptide can contain one or more of the following mutations: V1/V2 D133; V1/V2 K135; V1/V2 D137; V1/V2 S143; V1/V2 R146; V1/V2 E153 V1/V2 R166; V1/V2 K168; V1/V2 Q170; V3 R296; V3 S304; V3 R309; V3 R313; V3 F315; V3 V316; V3 Q326; V3 R325; β19 I418; β19 K419; β19 Q420; deletions involving V1/V2, V3, and/or β19 (including complete or partial deletions. See, e.g., Kwong et al., Nature, 393:649-659, 1998. Polypeptides can be produced routinely using suitable recombinant technologies.

III. Identifying Compounds Inhibiting HIV infection

Compounds inhibiting HIV infection can be identified by contacting a T-cell with a test agent, contacting the T-cell with infectious HIV under conditions effective for said HIV to latently infect said T-cell, activating the latently infected T-cell to produce an activated T-cell, and determining the amount of HIV produced from the activated T-cell, wherein the amount indicates whether the agent inhibits HIV infection; determining the amount of HIV produced from latently infected and activated T-cells which have been pre-treated with a test agent. The presence of HIV particles can be determined routinely, for example, by measuring polypeptides or RNA, such as p24, reverse transcriptase activity; viral RNA, etc. Such measurements can be made using immunoassays, PCR, etc.

The cell cytoskeleton can be used as an indicator of test agent efficiency. For example, phalloidin can be utilized to investigate the distribution of F-actin in cells by labeling phalloidin with fluorescent analogs and using them to stain actin filaments. A high-resolution technique can be used to detect F-actin at the light and electron microscopic levels with phalloidin conjugated to the fluorophore eosin which acts as the fluorescent tag. See, Capani et al., *J Histochem Cytochem.* 2001 November; 49(11):1351-61. In this method, known as fluorescence photo-oxidation, fluorescent molecules can be utilized to drive the oxidation of diaminobenzidine (DAB) to create a reaction product that can be rendered electron dense and detectable by light and electron microscopy.

The state of actin cytoskeleton also can be assayed using FITC-phalloidin, or other detectable phalloidin conjugates. Briefly, cells (such as primary T-cells) can be contacted with a suitable permeabilizing agent (e.g., triton). The cells can be washed and then contacted with FITC-phalloidin under conditions suitable for the phalloidin to bind to the actin filaments. The labeled cells can be fixed in paraformaldehyde, or other suitable fixative, and then visualized, e.g., using microscopy or flow cytometry. Pre-treatment of primary T-cells with HIV (or gp120 alone) results in less intense staining, indicating the actin network has been reduced, for example, by depolymerization, etc.

Specific examples are presented below of methods for detecting and treating and/or preventing HIV. They are meant to illustrate and not to limit the present invention.

EXAMPLE 1

Isolation of Resting CD4 T Cells from Peripheral Blood

Peripheral blood mononuclear cells (PBMC) were obtained from healthy donors at the Student Health Center, George Mason University (GMU), Fairfax, Va. All protocols involving human subjects were reviewed and approved by the GMU IRB. Resting CD4 T cells were purified by two rounds of negative selection as previously described in Wu and Marsh, *Science* 293(5534), 1503-6 (2001). Purified cells were cultured in RPMI 1604 medium supplemented with 10% heat-inactivated fetal bovine serum (Invitrogen, Carlsbad, Calif.), penicillin (50 U/ml) and streptomycin (50 µg/ml). Cells were rested overnight before infection or treatment.

EXAMPLE 2

Virus Preparation and Infection of Resting CD4 T Cells

Virus stocks of the HIV-1$_{NL4-3}$ (Adachi et al. *J Virol* 59(2), 284-91 (1986)) were prepared by transfection of HeLa cells with cloned proviral DNA as described in Wu and Marsh (2001). Supernatant was harvested at 48 hours, and filtered through a 0.45 µm nitrocellulose membrane. Virus titer (TCID50) was measured by infection of a Rev-CEM indicator cell line which was constructed through stable integration of a Rev-dependent GFP expression lentiviral vector into CEM-SS. This Rev-CEM cell line has no background GPF expression and gives titers close to those by using PBMC. For infection of resting CD4 T cells, viruses were first titrated to determine minimal levels detectable by p24 ELISA in replication assays described below. Unless specified, for most replication assays, $10^{3.5}$ to $10^{4.5}$ TCID50 units of HIV-1 were used to infect $10^6$ cells. For infection procedure, CD4 T cells were incubated with the virus for 2 hours, then washed twice with medium to remove unbound virus. Infected cells were resuspended into fresh RPMI 1604 medium supplemented with 10% heat-inactivated fetal bovine serum, penicillin (50 U/ml) and streptomycin (50 µg/ml) at a density of $10^6$ per ml and incubated for 5 days without stimulation. Cells were activated at day 5 with anti-CD3/CD28 magnetic beads at 4 beads per cells. For viral replication assay, 10% of infected cells were taken at 1, 3, 5, 6, 7, 8, 9 days post infection. Cells were pelleted and the supernatant was saved for p24 ELISA. Levels of p24 in the supernatant were measured by using Coulter HIV-1 p24 Assay Kit (Beckman Coulter, Inc. Miami, Fla.). Plates were kinetically read using ELx808 automatic microplate reader (Bio-Tek Instruments, Inc. Winooski, Vt.) at 630 nm.

EXAMPLE 3

Pre-treatment of Resting CD4 T Cells with Inhibitors

Resting CD4 T cells were treated with pertussis toxin (Sigma, St. Louis, Mo.) at a final concentration of 100 ng/ml for 2 hours, then infected with HIV-1. Following infection, cells were washed 2 to 3 times to remove cell-free virus and the inhibitor. Cells were treated with Jasplakinolide (Molecular Probes, Eugene, Oreg.) for 1 to 2 hours or Latrunculin A (Biomol, Plymouth Meeting, Pa.) for 5 minutes at various concentrations, washed twice with medium, then infected with HIV-1. Following infection, cells were washed twice to remove cell free virus. Cells were treated with 200 nM of Staurosporine (Biomol, Plymouth Meeting, Pa.) for 2 hours, then infected with HIV-1. Following infection, cells were washed twice to remove cell-free virus and the inhibitor.

To detect effects of Staurosporine on cofilin activation and actin depolymerization, cells were treated with 200 nM of Staurosporine for various times, then pelleted and lysed in NuPAGE LDS Sample Buffer (Invitrogen, Carlsbad, Calif.) for western blotting, or directly fixed and permeabilized for F-actin staining. For activation of resting CD4 T cells with PHA (3 µg/ml) (Sigma, St. Louis, Mo.) plus IL-2 (100 U/ml) (Roche Applied Science, Indianapolis, Ind.), cells were cultured in the presence of these agents for 1 day.

EXAMPLE 4

Pre-treatment of Resting CD4 T Cells with Synthetic Peptide

Synthetic peptide S3 (MASGVAVSDGVIKVFN; SEQ ID NO: 3) was derived from the N-terminal 16 amino acids of human cofilin and control peptide Q104 (WAPESAPLQSQM; SEQ ID NO: 4) was derived from human cofilin residues 104 to 115 with lysine 112 and 114 mutated to glutamine. Both peptides were synthesized by Celtek Peptides (Nashville, TN) and conjugated to a penetratin peptide (RQIKIWFQNRRMKWKK; SEQ ID NO: 5) for intracellular delivery. Resting CD4 T cells were treated with S3 or Q104 for 1 to 2 hours, then infected with HIV-1. Following infection, cells were washed 2 to 3 times to remove cell-free virus and the peptides.

EXAMPLE 5

Conjugation of Antibodies to Magnetic Beads and Stimulation of Resting CD4 T Cells Monoclonal antibodies again Human CD3 (clone UCHT1), CD28 (clone CD28.2), CD4 (clone PRA-T4) and CXCR4 (clone 12G5) were from BD Pharmingen (BD Biosciences, San Diego, Calif.). The anti-CD4, CXCR4 antibodies were selected for their shared epitopes with gp120. The CD4 antibody, clone RPA-T4, binds to the D1 domain of the CD4 antigen and is capable of blocking gp120 binding to CD4 (Dalgleish et al., Nature 312(5996), 763-7 (1984)), whereas the anti-CXCR4 antibody, clone 12G5, interacts with the CXCR4 extracellular loop 1 and 2 which partially overlap domains for the HIV-1 coreceptor function. Lu et al., Proc Natl Acad Sci USA 94(12), 6426-31 (1997). The 12G5 antibody also has been shown to block HIV-1 mediated cell fusion (Hesselgesser et al., J Immunol 160(2), 877-83 (1998)) and CD4-independent HIV-2 infection. Endres et al., Cell 87: 745-756 (1996). For conjugation, 10 µg of antibodies were conjugated with $4 \times 10^8$ Dynal beads (Invitrogen, Carlsbad, Calif.) for 30 min at room temperature. Free antibodies were washed away with PBS-0.5% BSA and magnetic beads were resuspended in 1 ml of PBS-0.5% BSA.

For stimulation of resting CD4 T cells, antibody conjugated beads were washed twice, then added to cell culture and rocked for 5 min. Conjugation of anti-CD4, CXCR4 antibodies with Streptavidin-labeled BD IMag particles (BD Biosciences, San Diego, Calif.) was carried out by using 25 µl of washed particles and 125 µl of biotin-labeled anti-CD4, CXCR4 antibodies (BD Biosciences, San Diego, Calif.). The mixture were incubated for 30 min at room temperature with gentle shaking, and washed three times and resuspended into 250 µl of PBS-0.1% BSA. Resting CD4 T cells were treated at 10 µl particles per $10^6$ cells.

EXAMPLE 6

FITC-Phallodin Staining of F-actin and Flow Cytometry

Cells were stimulated with HIV-1 or gp120 IIIB (Microbix Biosystems Inc. Toronto, Ontario). F-actin staining using FITC-labeled phalloidin (Sigma, St. Louis, Mo.) was carried out according to the manufacture's recommendation with minor modifications. Briefly, each staining was carried out by using $10^6$ cells. Cells were pelleted, fixed and permeabilized with cytoperm/cytofix (BD biosciences, San Diego, Calif.) for 20 min on ice, followed by stained with 5 µl of 0.3 uM FITC-labeled phalloidin for 30 min at 4° C. After wash, cells were resuspended in 1% paraformaldehyde and analyzed on FACSCalibur (BD Biosciences, San Jose, Calif.)

EXAMPLE 7

Staining of LAF-1 Activation on Resting CD4 T Cells

Half million CD4 T cells in 500 µl culture medium were treated with 5 µl of human IgG (Jackson Immuno Research, West Grove, Pa.) to block non-specific staining. Cells were stained with 10 µl (50 µg/ml) of human ICAM-1 Fc chimera (R&D System, Minneapolis, Minn.) for 20 min at 4° C. Cells were washed and blocked by 5 µl of mouse IgG (Jackson ImmunoResearch, West Grove, Pa.), followed by the addition of 10 µl of FITC labeled mouse anti-human Fc (Jackson ImmunoResearch, West Grove, Pa.), and incubated for 20 min at 4° C. Cells were finally washed and resuspended in 500 µl of 1% paraformaldehyde for flow cytometry.

EXAMPLE 8

Confocal Microscopy

Stained cells were imaged using a Zeiss Laser Scanning Microscope (Thornwood, N.Y.), LSM 510 META, with a 40 NA 1.3 or 60 NA 1.4 oil Dic Plan-Neofluar objective. Samples were excited with two laser lines, 488 nm for GFP and 543 nm for Alexa 594. Images were simultaneously recorded in three channels: channel one: fluorescent emissions from 505 to 530 nm for GFP (green); channel two: emissions from 580 to 650 nm for Alexa 594 (red); channel three: DIC. Images were processed and analyzed by the LSM 510 META software.

Figure 8:
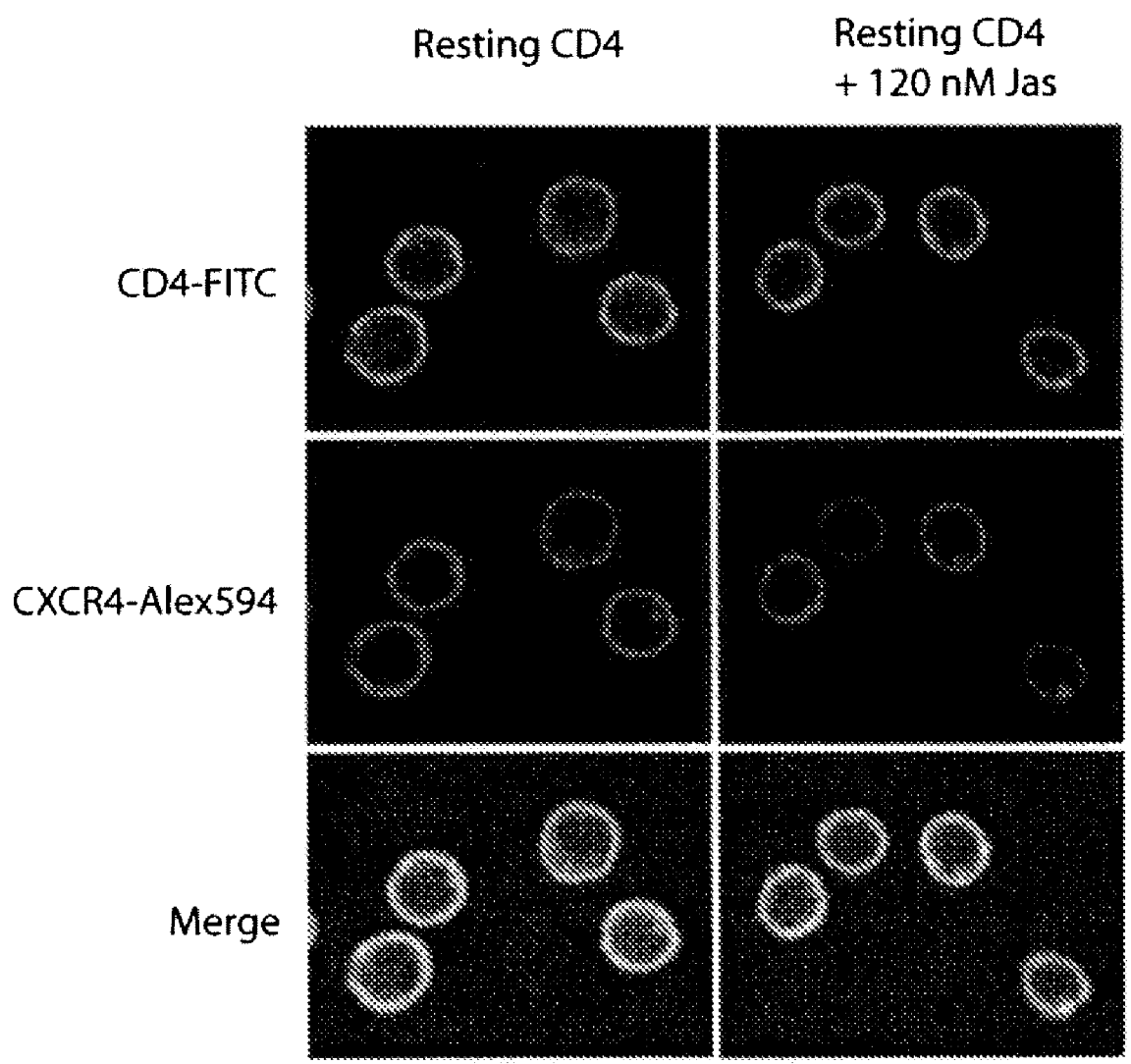
FIG. 8: Confocal microscopy of CD4 and CXCR4 distribution on resting CD4 T cells treated with 120 nM Jas.

FIG. 8 illustrates confocal microscopy of CD4 and CXCR4 distribution on resting CD4 T cells treated with 120 nM Jas. Resting CD4 T cells were treated with 120 nM of Jas for 2 hours, then fixed and stained with a FITC-labeled anti-human CD4 monoclonal antibody and a biotin-labeled anti-human CXCR4 monoclonal antibody followed by Alexa Fluor-594 labeled streptavidin (right panel). Untreated resting CD4 T cells were used as a control (left panel).

EXAMPLE 9

PCR Amplification

To remove plasmid DNA contamination, viral stock was treated with Benzonase (Novagen, Madison, WI) (250 U/ml) at 370° C for 15 min before infection. Total cellular DNA were purified using SV total RNA isolation kit as recommended by the manufacture (Promega, Madison, WI). For detection of viral late reverse transcription products by PCR, forward primer HIV/Tat-Rev-5' (5'GGTTAGACCAGATCT-GAGCCTG 3'; SEQ ID NO: 6) and reverse primer LTR-gag2 (5'TTAATACCGACGCTCTCGCACC 3'; SEQ ID NO: 7) were used. PCR was carried out in 1× Ambion PCR buffer, 125 µM dNTP, 50 pmol each primer, 1U SuperTaq Plus (Ambion Inc. Austin, TX) with 30 cycles at 94° C. for 20 seconds, 68° C. for 60 seconds. For relative quantification, the cellular-actin pseudogene were co-amplified using QuantumRNA-actin Internal Standards (Ambion Inc. Austin, TX), with a ratio from 5/5 to 1/9 for actin primer/competitor.

EXAMPLE 10

Cofilin and Phospho-Cofilin Western Blot

Briefly, $10^6$ of CD4 T cells were lysed in NuPAGE LDS Sample Buffer (Invitrogen, Carlsbad, Calif.) followed by sonication. Samples were heated at 70° C. for 10 minutes before loading, then separated by SDS-PAGE and transferred onto nitrocellulose membranes (Invitrogen, Carlsbad, Calif.). The membranes were washed in TBS for 5 minutes and then blocked for 30 minutes at room temperature with Starting Block blocking buffer (Pierce, Rockford, Ill.). The blots were incubated with either a rabbit anti-cofilin antibody (1:1000 dilution) (Cell Signaling, Danvers, Mass.) or a rabbit anti-phospho-cofilin (ser3) antibody (1:1000 dilution) (Cell Signaling, Danvers, Mass.) diluted in 5% BSA-TBST and rocked at room temperature for 1 hour. The blots were washed three times for 15 minutes each and then incubated with a goat anti-rabbit horseradish peroxidase-conjugated antibodies (KPL, Inc. Gaithersburg, Md.) diluted in 2.5% skim milk-TBST (1:1000) for 1 hour. The blots were washed again three times for 15 minutes each and then developed with SuperSignal west femto maximum sensitivity substrate (Pierce, Rockford, Ill.). Images were captured with a CCD camera (Fluor Chem 9900 Imaging Systems) (Alpha Innotech, San Leandro, Calif.) and analyzed and processed by NIH-Image Version 163.

EXAMPLE 11

G-actin/F-actin Fractionation and F-actin/Cofilin Cosedimentation Assays

G-actin/F-actin cellular fractions were prepared using the G-actin/F-actin in vivo assay Kit (Cytoskeleton, Inc, Denver, Co). Briefly, 2 million resting CD4 T cells per sample were treated with 500 pM gp120 from 5 minutes to 1 hour. The cells were harvested by centrifugation at 2,000 g for 1 minute at 37° C. and then resuspended in 1.5 ml lysis buffer (50 mM PIPES pH6.9, 50 mM KCl, 5 mM MgC12, 5 mM EGTA, 5% (v/v) Glycerol, 0.1% Nonidet P40, 0.1% Triton X-100, 0.1% Tween 20, 0.1% 2-mercapto-ethanol, 0.001% Antifoam C and 4 uM Tosyl arginine methyl ester, 15 uM Leupeptin, 10 uM Pepstatin A, 10 mM Benzamidine and 1 uM ATP). The lysates were homogenized with a 200 µl fine orifice pipette and then placed at 37° C. for 10 minutes. The lysates were then centrifuged at 420 g for 5 minutes to remove cell debris and the supernatant was collected and centrifuged at 100,000 g at 37° C. for 1 hour. Following centrifugation, the supernatant containing G-actin was saved and the pellet containing F-actin was resuspended in F-actin depolymerizing solution (10 µM cytochalasin D) and incubated on ice for 1 hour with occasional pipetting. Equal volumes of the supernatant and the pellet factions were used for SDS PAGE and western blotting for actin. For the F-actin/cofilin cosedimentation assay, the F-actin pellet was directly resuspended in 1×LDS sample buffer for SDS-PAGE and western blotting for cofilin and actin.

EXAMPLE 12

NEPHGE and Western Blot for Cofilin

One-dimensional NEPHGE was performed as previously described in Nebl et al. *Cell Signal* 16(2), 235-43 (2004)). Briefly, resting T cells were lysed in TKM buffer (50 mM Tris pH 7.6, 25 mM KCL, 5 mM $MgCL_2$, 1 mM Na-Vandate, 5 mM NaF, 20 ug/ml Leupeptin, 20 ug/ml Aprotinin, 0.3 uM okadaic acid containing 0.5-1% NP-40) and sedimented at 20,800 g for 10 minutes at 4° C. Postnuclear fraction was collected and used for the detection of cofilin. NEPHGE were performed with 6%-focusing slab gel with 5% Ampholines pH 3 to 10 (Invitrogen, Carlsbad, Calif.). The gels were run for 1 hour at 100V, 2 hours at 250V and 2 hours at 300V, then transferred onto nitrocellulose membrane (Invitrogen, Carlsbad, Calif.) and incubated with 1:1000 dilution of a rabbit anti-cofilin antibody (Cell Signaling, Danvers, Mass.), followed by incubation with 1:1000 dilution of a goat anti-rabbit antibody conjugated with horseradish preoxidase (KPL, Gaithersburg, Md.). Signals were acquired by using Super-Signal west femto maximum sensitivity substrate (Pierce, Rockford, Ill.) and a CCD camera (FluorChem 9900 Imaging Systems) (Alpha Innotech, San Leandro, Calif.). Images were analyzed and quantified using NIH-Image Version 163 as suggested by the software developer.

EXAMPLE 13

In Vitro LIMK Kinase Assay

LIMK1 Kinase assays were performed using purified LIMK1 and GST-tagged recombinant human cofilin (Upstate Biotechnologies, Lake Placid, N.Y.) according to the manufacture's recommendation with minor modifications. Briefly, 18 µg of recombinant cofilin was incubated in 1× Kinase reaction buffer (800 nM MOPS-NaOH, pH7.0, 200 µM EDTA) in the presence or absence of Staurosporine (200 nM) or the S3, Q104 peptides. LIMK1 was serially diluted in dilution buffer (20 mM MOPS-NaOH pH 7.0, 1 mM EDTA, 0.01% Brij-35, 5% glycerol, 0.1% 2-ME, 1 mg/ml BSA), then added into the reaction along with the ATP buffer (10 mM Magnesium Acetate, 100 µM ATP). The reaction was incubated for 15 minutes at 30° C. with constant agitation. The reaction was stopped by adding 25% (V/V) of 4×LDS sample buffer for SDS-PAGE and heated for 10 minutes at 70° C. Cofilin phosphorylation was analyzed by SDS-PAGE and western blotting using a rabbi anti-phospho-cofilin (ser3) antibody (Cell Signaling, Danvers, Mass.) as described in Example 10.

EXAMPLE 14

IL-2 ELISA

IL-2 release into cell culture supernatant was detected by a human IL-2 ELISA development kit (PeproTech, Rocky Hill, N.J.) according to the manufacture's instruction. Briefly, each well of a plate was coated with 100 µl of capture antibody (1 µg/ml) and incubated overnight at room temperature, then washed and blocked with 300 µl of blocking solution for one hour at room temperature. Samples in plates were incubated for 1 hour at 37° C., then washed and incubated with 100 µl of detection antibody (0.5 µg/ml) for 1 hour at 37° C. Plates were washed and incubated with 100 µl of the avidin-peroxidase conjugate (1:2000 dilution) for 30 minutes at room temperature followed by washing and incubation with 100 µl of Tetramethylbenzidine (TMB) substrate buffer. Plates were kinetically read using ELx808 automatic microplate reader (Bio-Tek Instruments, Inc. Winooski, Vt.) at 630 nm.

EXAMPLE 15 gp120 Induces Cytoskeletal Rearrangement

To determine the nature of the cytoskeletal rearrangement induced by gp120, filamentous actin (F-actin) change was compared following treating resting T cells with SDF-1, the natural ligand for CXCR4, or with gp120. In SDF-1 treated cells rapid actin polymerization (FIG. 1A) was observed with a characteristic of highly polarized cortical actin (12) (FIG. 1C). Conversely, in gp120 treated cells, actin depolymerization started at 5 mm and became more pronounced at 1 to 3 hours (FIG. 1B). Depolymerization was consistently observed in multiple donors and across a range of gp120 concentrations below 50 mM.

As shown in FIG.1, HIV-1 gp120 mediates depolymerization of cortical actin in resting CD4 T cells. FIG. 1B shows actin depolymerization by gp120. Cells were treated with gp120IIIB (50 nM) and stained with FITC-phalloidin and analyzed by flow cytometer. Shown is histogram. FIG. 1A shows actin polymerization by SDF-1. Cells were treated with SDF-1 (50 ng/ml) and stained with FITC-phalloidin. FIG. 1C shows confocal microscopy of resting T cells treated with SDF-1 (50 ng/ml), HIV-1 (ng of p24) or gp120 (50 nM), respectively and stained with FITC-phallodin. Images were acquired in identical condition. Red arrows indicate localized actin polymerization induced by SDF-1 or gp120. FIG. 1D shows HIV-1 mediated cortical actin depolymerization. The bright resting T cell (untreated control) and the dime cell (HIV-1 treated) were selected and compared. The relative intensity of F-actin staining was measured along the red arrow lines (n=1,000 measurements per line) and plotted at the bottom. The major difference detected was in the cortical actin region. FIG. 1E shows cytosolic (non-cortical) F-actin staining between HIV-1 treated and untreated cells detected no difference. The intensity of cytosolic F-actin staining in randomly selected cells (equal number of infected versus uninfected) was measured along the folded red lines (n=1,000 measurements per line) and shown as the mean ±SD on the right (P>0.117, n=20,000).

These data suggest distinct differences between SDF-1 and gp120 in stimulating cellular responses, despite their shared similarities in CXCR4 binding. K. Balabanian et al., *J Immunol* 173, 7150 (2004). While SDF-1 triggers physiological responses, gp120 likely mediates aberrant signaling with potential pathogenic consequences. Additionally, unlike SDF-1, gp120 engages both CXCR4 and CD4.

EXAMPLE 16 gp120 Depolymerizes Actin

Figure 7:
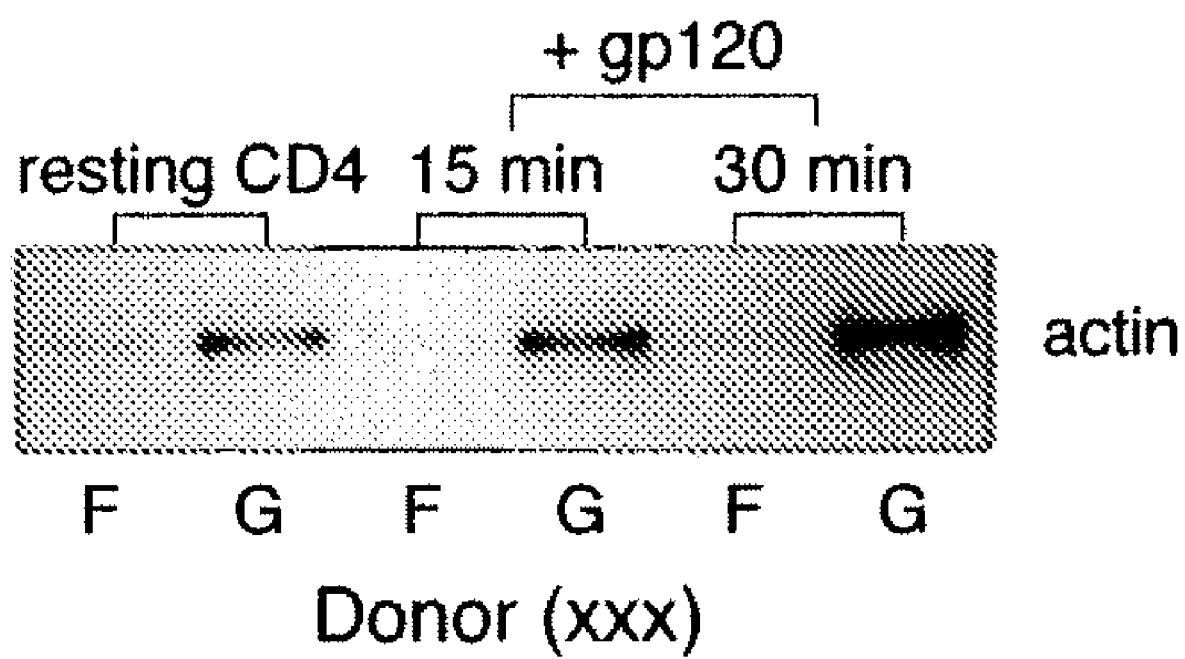
FIG. 7: Cytoskeletal actin fractionation of resting CD4 T cells treated with gp120.

To further confirm actin depolymerization by gp120, cellular fractionation was performed to measure changes in the ratio of F-actin to globular actin monomer (G-actin) in response to gp120 treatment. There was a significant increase in the G/F actin ratio following gp120 treatment, consistent with the data from FITC-phalloidin staining (FIG. 7). Finally, confocal microscopy revealed that the actin depolymerization in HIV treated cells mainly occurred in the cortical actin region in resting CD4 T cells (FIG. 1D). No significant difference was observed in the intracellular F-actin staining beyond the cortical actin between treated and untreated cells (FIG. 1E). Thus, HIV-1 gp120 largely depolymerizes the cortical actin in resting T cells.

EXAMPLE 17

CD4 and CXCR4 in gp120 Mediated Actin Depolymerization

Figure 2:
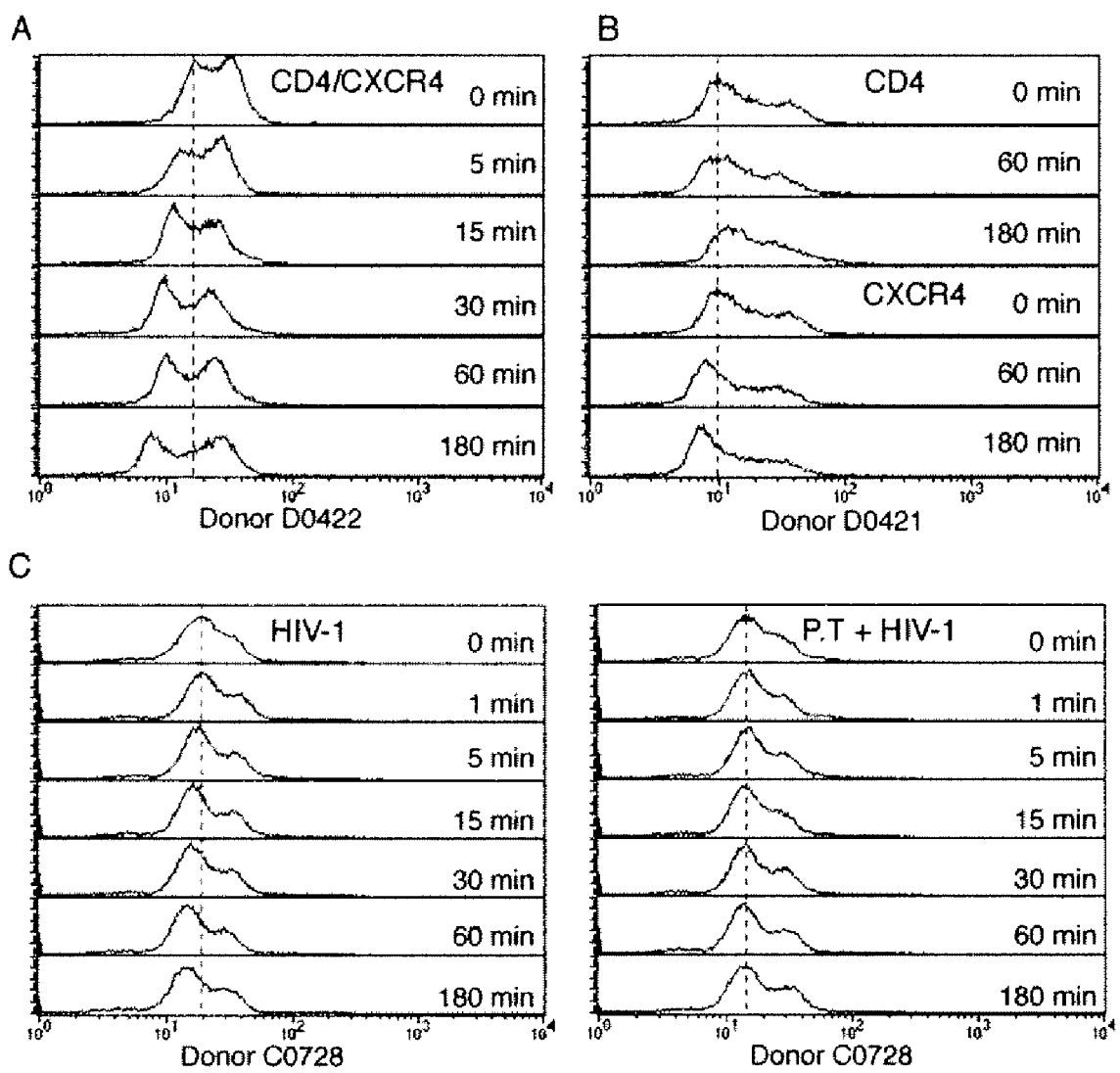
FIG. 2: HIV gp120-CXCR4 signaling triggers P.T-sensitive actin depolymerization.

To define specific roles of CD4 and CXCR4 in gp120 mediated actin depolymerization, resting T cells were stimulated with magnetic particles coated with antibodies against both receptors. FIG. 2. illustrates that HIV gp120-CXCR4 signaling triggers P.T-sensitive actin depolymerization. (A) Actin depolymerization by anti-CD4/CXCR4 antibodies conjugated to BD IMag particles. (B) Actin depolymerization by anti-CXCR4 but not anti-CD4 BD IMag particles. (C) HIV-1 mediated actin depolymerization was dependent on P.T-sensitive signaling. Cells were not treated (left panel) or treated with P.T (right panel), followed by HIV-1 infection (ng of p24 per $10^6$ cells) and staining with FITC-phallodin for F-actin.

FIG. 2A shows actin depolymerization following antibody stimulation. When cells were stimulated with either anti-CD4 or anti-CXCR4 particles, actin depolymerization occurred only with CXCR4 stimulation, while CD4 stimulation slightly enhanced actin polymerization (FIG. 2B). Thus, CXCR4 is sufficient to mediate actin depolymerization. Notably, the ability of these antibodies to induce actin depolymerization correlates with their ability to enhance viral replication.

EXAMPLE 18

Gαi-Mediated Actin Depolymerization

Actin polymerization induced by SDF-1 is regulated through binding to CXCR4 and subsequent activation of the G proteins (M. P. Grump et at., *Embo J* 16, 6996 (1997); X. Huang a at., *Biophys J* 84, 171(2003)), particularly pertussis toxin (P.T) sensitive Gαi (Y. Sotsios, et al., *Journal of Immunology* 163, 5954 (1999)). To determine whether the depolymerization induced by gp 120 is likewise mediated through Gαi, resting T cells were treated with P.T and found that P.T completely inhibited viral induced actin depolymerization (FIG. 2C), suggesting that the depolymerization also is mediated through CXCR4 and the Gαi protein. While the same receptor mediates both actin polymerization and depolymerization, SDF-1 has been reported to both attract and repel T cells depending on dosages. M. C. Poznansky et at., *Nat Med* 6, 543 (2000). The fact that P.T inhibited viral replication as well as actin depolymerization suggests that the depolymerization could be one of the essential functions of gp120-CXCR4 signaling in priming viral latent infection of resting T cells.

EXAMPLE 19

Effect of Jas on T Cell Activity

To test whether cortical actin in resting T cells is a barrier that needs to be depolymerized, a F-actin stabilizing agent's, jasplakinolid (Jas), ability to interfere with HIV envelope-induced actin depolymerization was evaluated. Similar to phalloidin, Jas binds to F-actin irreversibly and stabilizes actin filaments M. R. Bubb, et al., *J Biol Chem* 275, 5163 (2000). Given that the actin cytoskeleton also is involved in T cell activation, Jas may affect HIV replication indirectly by affecting T cell activity. For instance, the actin cytoskeleton is known to be the driving force for receptor clustering and the formation of the supramolecular activation cluster (SMAC) during T cell activation. C. Wulfing and Davis, M. M., *Science* 282, 2266 (1998). This process involves the actin-dependent activation of LFA-1 (Y. van Kooyk, et al., *J Biol Chem* 274, 26869 (1999); M. L. Dustin and T. A. Springer, *Nature* 341, 619 (1989)), which is required for sustained signaling to reach full T cell activation. C. Wulfing, et al., *Proc Natl Acad Sci USA* 95, 6302 (1998).

Thus, the effect of Jas on T cell activity was determined. FIG. 3A illustrates inhibition of HIV-1 latent infection by Jas. Effects of Jas on LFA-1 activation also were tested. Jas treated or untreated resting T cells were activated by anti-CD3/CD28 bead and stained with human ICAM-1/Fc chimera and analyzed by flow cytometer. The effects of Jas on IL-2 secretion also were measured. FIG. 3A shows the effects of Jas on HIV-1 latent infection of resting T cells. Cells were treated with Jas for 2 hours, washed, infected with HIV-1 for 5 days, then activated by anti-CD3/CD28 bead. FIG. 3B shows the effects of Jas on viral entry. Following infection, cellular DNA was PCR amplified for viral late DNA and β-actin pseudogene. The effects of Jas on HIV-1 infection of pre-activated T cells are shown in FIG. 3C. Cells were pre-activated with PHA plus IL-2, then treated and infected as in FIG. 3A. FIG. 3D shows the effects of Jas on HIV-1 infection of transformed cells. CEM-SS cell were treated and infected as in FIG. 3A. Effects of Jas on HIV-1 infection of resting T cells pre-stimulated with anti-CD4/CXCR4 bead (2 beads/cell) are shown in FIG. 3E. Pre-stimulated cells were treated and infected as in FIG. 3A.

Staining of resting T cells with ICAM-1,the ligand for active LFA-1, confirmed that T cell activation induced LFA-1 activation. However, treatment of T cells with 3 1µM Jas greatly inhibited LFA-1 activation. Therefore, Jas was titrated to lower dosages. It was found that at 120 nM and below, Jas has no detectable inhibition on LFA-1 activation. Using secretion of IL-2 as a second indicator for T cell activity, it was confirmed that at 120 nM and below, Jas had no significant effect on IL-2 secretion although at 600 nM and above it inhibited IL-2 expression following T cell activation. Effects of Jas on T cell activity were further tested by cell cycle analysis. At 3 µM, Jas arrested cells in S phase, whereas at 120 nM, no cell cycle arrest was observed (data not shown).

From these results, it was determined that a Jas concentration below 120 nM could be used to test its effects on HIV replication (FIG. 3A). At 120 nM, Jas retains the characteristics of irreversible binding to F-actin and significantly inhibited the subsequent competitive binding of phalloidin (data not shown). Given its minimal impact on T cell activity at lower dosages, Jas was used to treat resting T cells for 2 hours, then cells were infected. Complete inhibition of HJV replication was observed at 600 and 120 nM and partial inhibition at 24 nM (FIG. 3A). Jas inhibition was observed in multiple donors (data not shown) and the inhibition was not due to inhibition of gp120 mediated CD4/CXCR4 receptor clustering which has been suggested to be actin dependent. S. Iyengar, et al., *J Virol* 72, 5251 (1998). Confocal microscopy did not reveal any significant difference in CD4/CXCR4 distribution on the surface between 120 nM Jas treated and untreated cells (FIG. 8). Neither was the inhibition due to effects on viral-cell fusion which also has been suggested to be actin dependent. S. E. Pontow, et al., *Journal of Virology* 78, 7138 (2004). Quantitative PCR amplification of intracellular viral DNA did not detect any difference between 120 nM Jas treated and untreated cells, suggesting that the inhibition was not at the entry level (FIG. 3B).

Figure 3:
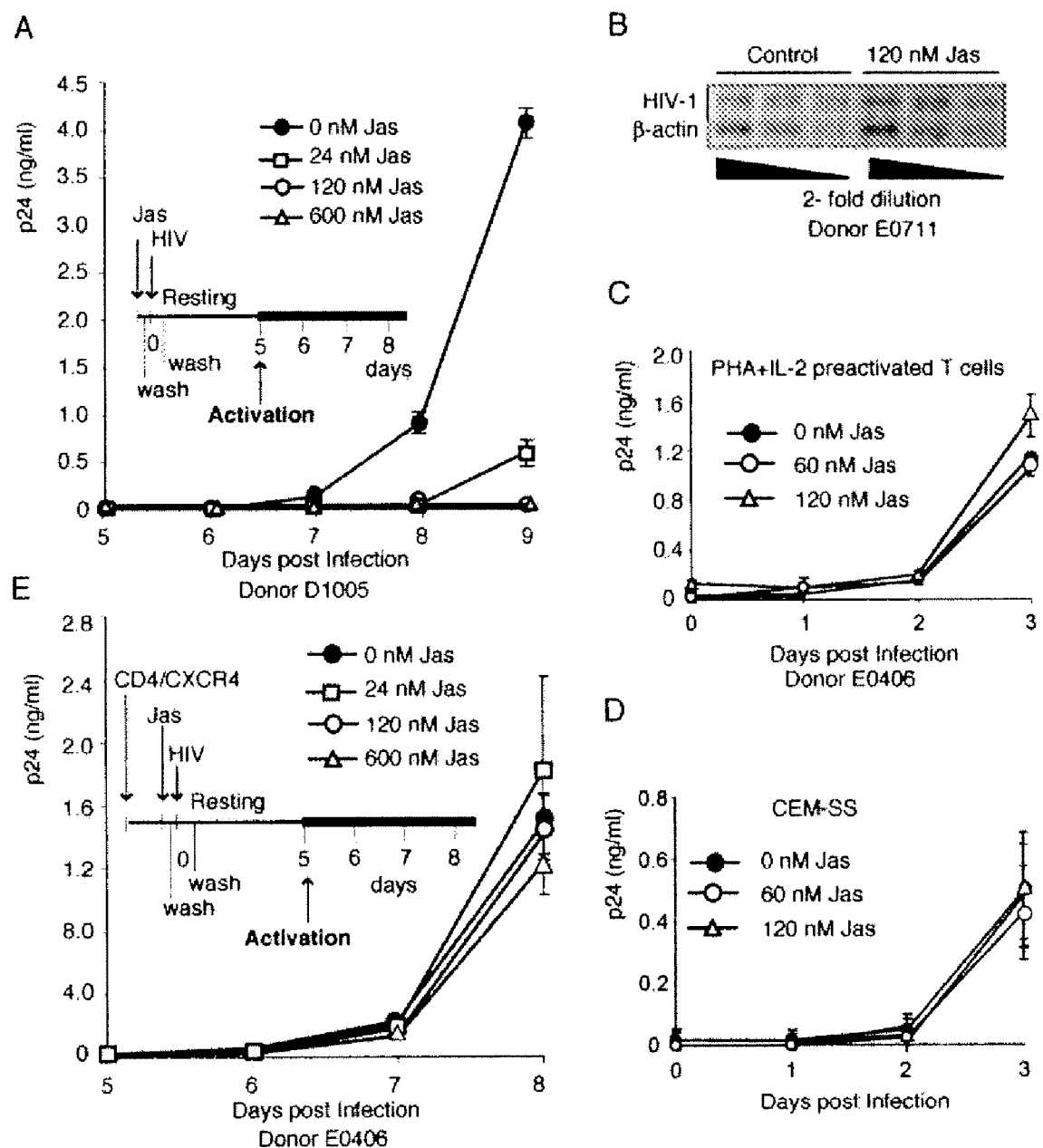
FIG. 3: Inibition of HIV-1 laten infection by Jas.

These results show that actin rearrangement mediated by the HIV envelope is critical for a post entry process, such as uncoating or intracellular migration. Contrary to resting CD4 T cells, similar Jas treatment of transformed CEM-SS or pre-activated T cells had no inhibition on HIV replication (FIG. 3, C and D). It is likely that at 120 nM, Jas has no inhibition on actin remodeling mediated by cell cycle. At a higher dosage (3µM), however, when cell cycle was arrested, Jas did inhibit HIV replication in GEM-SS (data not shown). These data also confirm that at 120 nM, Jas does not affect viral entry or reverse transcription (FIG. 3B). Also, pre-stimulation of resting T cells with CD4/CXCR4also completely abolished the inhibition by 120 nM Jas, suggesting that the actin cytoskeleton in resting T cells may no longer be a barrier once reorganized by the CD4/CXCR4 pre-stimulation (FIG. 3E).

EXAMPLE 20

Effect of Lat-A on T Cells

To further confirm that the cortical actin cytoskeleton constitutes a restriction in resting T cells, another actin inhibitor, Latraculin A (Lat-A) was investigated, which has been shown to specifically induce actin depolymerization without affecting microtubules. I. Spector, et al., *Science* 219, 493 (1983); M. Coue, et al., *FEBS Lett* 213, 316 (1987); and K. R. Ayscough et al., *J Cell Biol* 137, 399 (1997). Unlike Jas, Lat-A does not directly interact with F-actin to promote actin disassembly (Ayscough (1997)), rather it binds to G-actin reversibly and inhibits its assembly into filamentous actin. Spector (1983); Ayscough (1997).

It was speculated that artificial induction of actin depolymerization by Lat-A may enhance HIV replication if cytoskeletal actin serves as a barrier. To test this, Lat-A was titrated at various dosages from 2.5 µM to 2.5 nM, and actin depolymerization was examined in resting CD4 T cells.

Figure 4:
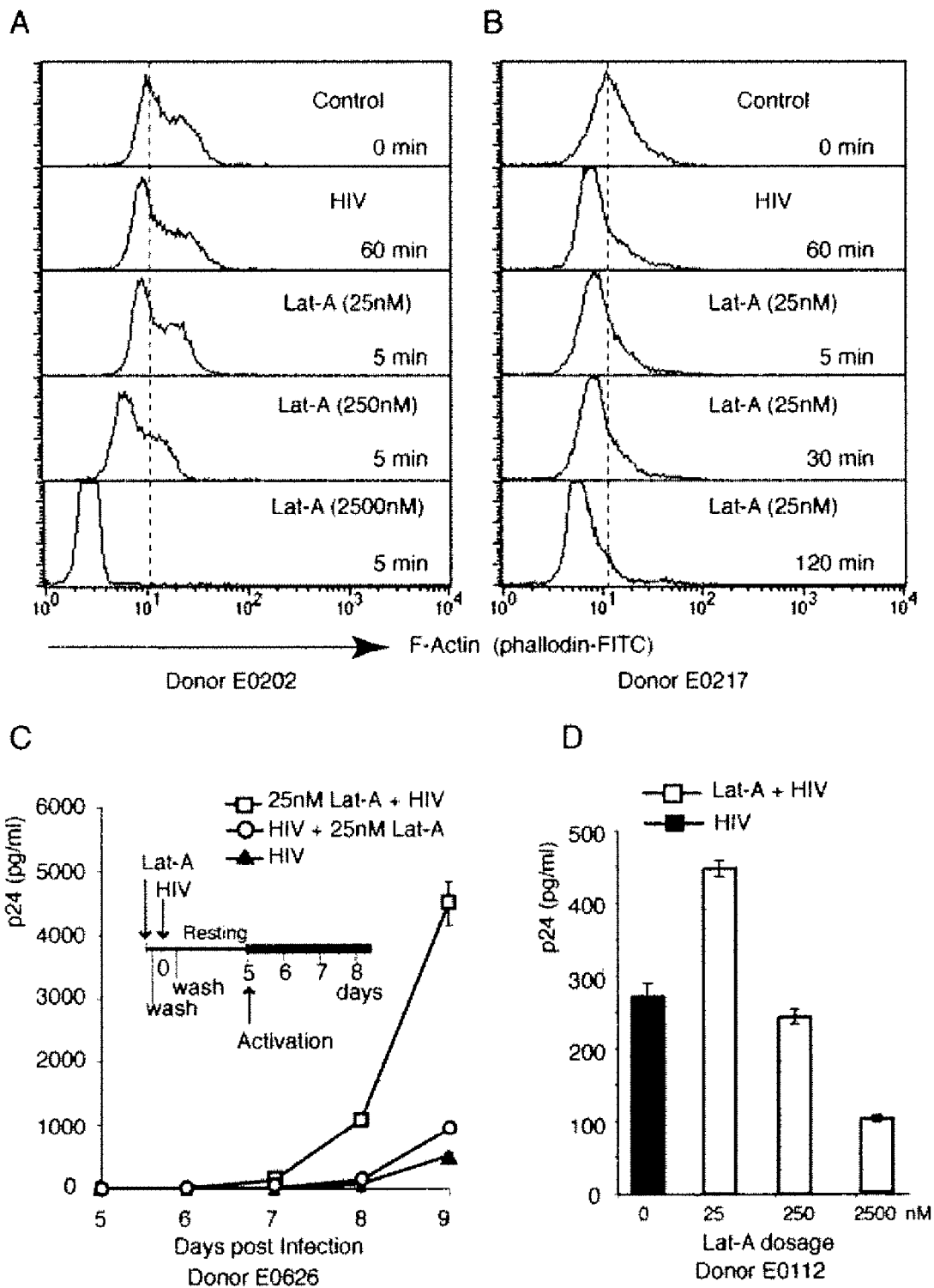
FIG. 4: Effects of Lat-A on actin depolymerization and HIV-1 replication in resting CD4 T cells.

FIG. 4. shows the effects of Lat-A on actin depolymerization and HIV-1 replication in resting CD4 T cells. FIG. 4A shows dose-dependent actin depolymerization by Lat-A. Cells were treated with Lat-A for 5 min, then stained for F-actin and analyzed by flow cytometer. Untreated and HIV-1 treated cells were used as controls. FIG. 4B displays time-dependent actin depolymerization by Lat-A. Cells were treated with 25 nM Lat-A for various times, stained and analyzed as in FIG. 4A. Enhancement of HIV-1 latent infection by Lat-A is shown in FIG. 4C. Cells were treated with 25 nM Lat-A for 5 minutes, washed, infected with HIV-1 for 5 days, then activated with anti-CD3/CD28 bead. As a control, cells were also treated with Lat-A for 5 minutes after infection. FIG. 4D shows dose-dependent enhancement of viral replication by Lat-A. Resting CD4 T cells were treated with different dosages of Lat-A for 5 minutes, then infected and activated as in FIG. 4C.

At high doses (2.5 µM to 250 nM), Lat-A induced dramatic actin depolymerization, whereas at a lower dose (25 nM) it induced actin depolymerization to an extent similar to that induced by HIV-1 (FIG. 4A). Thus, resting T cells were pre-treated with 25 nM Lat-A, then infected with HIV-1. Enhanced HIV replication by 25 nM Lat-A was observed in all donors examined (FIG.4C).

Importantly, this enhancement was seen only in cells pre-treated with Lat-A prior to infection (FIG. 4C). These results demonstrate that artificial depolymerization before infection enhances HIV infection. The effects of Lat-A at higher dosages were also tested where Lat-A induced actin depolymerization was much greater than the physiological depolymerization induced by HIV-1 (FIG. 4D). Interestingly, at 250 nM, donor-dependent variations from enhancement to inhibition occurred (data not shown). At 2.5 µM, however, Lat-A inhibited viral replication in all donors (FIG. 4D). These results show that excessive, non-physiological depolymerization can affect T cell function. Thus, besides being a barrier, the cytoskeleton may actively participate in post entry processes. Thus excessive depolymerization can affect viral function.

Thus, the stabilization of actin by Jas inhibits HIV replication, whereas depolymerization of actin by Lat-A or CD4/CXCR4 beads enhances viral replication. Collectively, these findings show that in resting CD4 T cells, actin cytoskeleton represents a barrier that needs to be dynamically reorganized to some extent and that HIV-1 exploits the CXCR4 signaling pathway to fulfill this requirement.

EXAMPLE 21

Cofilin Activity in Resting CD4 T Cells and HIV-1 Infected Cells

Given that HIV-1 envelope-CXCR4 signaling mediates actin depolymerization, cofilin activity was compared in resting CD4 T cells and cells infected with HIV-1.

Figure 5:
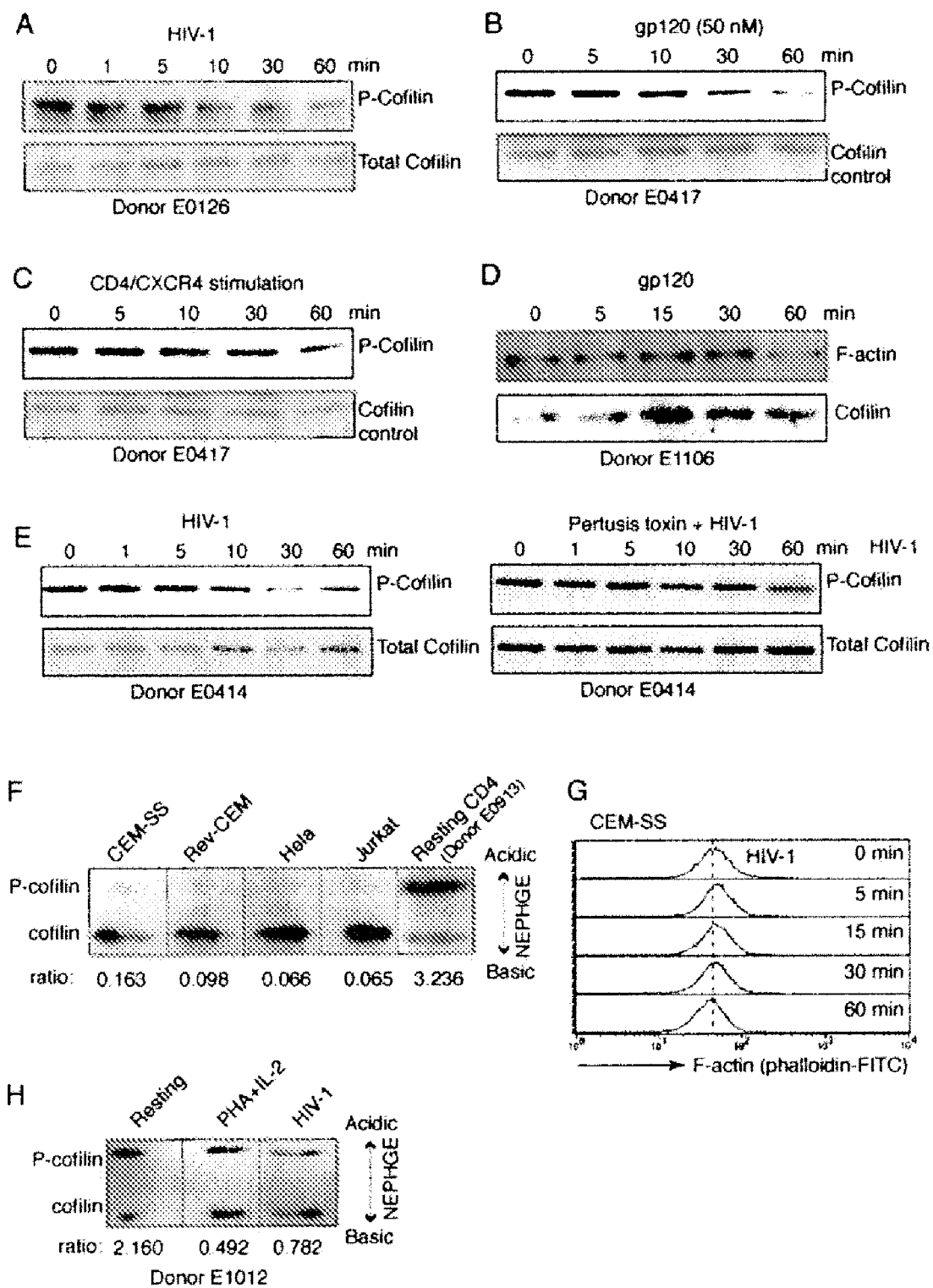
FIG. 5: HIV gp120-CXCR4 signaling triggers P.T-sensitive activation of cofilin, FIG. 5A provides Western blots of HIV-1 treated cells probed for P-cofilin, then stripped and reprobed for total cofilin.

FIG. 5. shows that HIV gp120-CXCR4 signaling triggers P.T-sensitive activation of cofilin. Western blots of HIV-1 treated cells were probed for P-cofilin, then stripped and reprobed for total cofilin (FIG. 5A). FIG. 5B shows activation of cofilin by gp120. Activation of cofilin by anti-CD4/CXCR4 bead (two beads/cell) is shown in FIG. 5C. FIG. 5D shows activation of cofilin by gp120 promotes its association with actin cytoskeleton. F-actin fractions were prepared from gp120 treated resting T cells and immunoblotted for actin (upper band) and cofilin (lower band). FIG. 5E shows P.T-sensitive activation of cofilin by HIV-1. Cells were not treated (left panel) or treated (right panel) with P.T then infected and analyzed as in FIG. 5A. FIG. 5F shows constitutive activation of cofilin in transformed cell lines. P-cofilin (upper band) and active cofilin (lower band) was separated by NEPHGE-western blotting and the relative ratio of P-cofilin to active cofilin was indicated at the bottom. Resting CD4 T cells were used as a control at the right end. F-actin staining of CEM-SS cells infected with HIV-1 is shown in FIG. 5G. Cofilin activation induced by PHA plus IL-2 and HIV-1 treatment of resting CD4 T cells is displayed in FIG. 5H In resting CD4 T cells, cofilin was largely inactivated by phosphorylation, and upon HIV infection, was activated by dephosphorylation within minutes (FIG. 5A). HIV-induced cofilin activation was seen in all donors examined. The kinetics correlate well with HIV-1 induced actin depolymerization, with strong cofilin activation and actin depolymerization occurring between 1 to 2 hours (FIG. 2C).

To confirm that cofilin activation was triggered by HIV envelope binding, resting CD4 T cells were treated with gp120. Again, cofilin was activated by gp120 (FIG. 5B). Furthermore, anti-CD4/CXCR4 magnetic bead stimulation of resting CD4 T cells results in cofilin activation (FIG. 5D). These data demonstrated that HIV-1 envelope engagement of the CD4/CXCR4 receptors is sufficient to activate cofilin in resting T cells. To demonstrate the association of active cofilin with F-actin in gp120 stimulated resting T cells, F-actin was fractionated before and after gp120 treatment. Low level cosedimentation of cofilin with F-actin was observed in resting T cells (FIG. 5D). Upon gp120 stimulation, there was a significant increase in cofilin association with F-actin, followed by a decrease in F-actin at 1 hour (FIG. 5D). These data confirm that activation of cofilin by gp120 promotes its association with F-action and subsequent actin depolymerization.

To determine whether cofilin activation is from the Gαi dependent CXCR4 signaling, resting CD4 T cells were pretreated with P.T and then infected with HIV-1. Complete inhibition of cofilin activation was observed by peltussis toxin (FIG. 5E). This is consistent with P.T inhibition of actin depolymerization by HIV-1. Thus, HIV envelope binding to CXCR4 triggers P.T sensitive activation of cofilin and its association with F-actin to promote actin dynamics.

EXAMPLE 22

Cofilin Activation Mediated by CXCR4 Signaling

Contrary to resting CD4 T cells, transformed T cells do not require CXCR4 signaling to support viral replication. However, binding of gp120 to CXCR4 does trigger signaling cascades resulting in $Ca^{2+}$ mobilization (B. J. Doranz et al., *J Virol* 73, 2752 (April, 1999)) and activation of signaling molecules such as Pyk2 in cell lines. C. B. Davis et al., *Journal of Experimental Medicine* 186, 1793 (1997). Thus, it was investigated if CXCR4 signaling also leads to the activation of cofilin in these cells.

Using nonequilibrium pH gel electrophoresis (NEPHGE) (P. Z. O'Farrell, et al., *Cell* 12, 1133 (1977)), basal levels of active cofilin were measured in transformed cells. In great contrast to resting CD4 T cells in which cofilin is largely in the inactive form, transformed T cells predominately carry active cofilin (FIG. 5F). These results show that in transformed cells, cofilin is constitutively active (Y. Samstag et al., *Proc Natl Acad Sci USA* 91, 4494 (1994)) and that activation through CXCR4 is no longer needed for the virus. Consistently, treatment of transformed CEMSS T cells with HIV-1 did not induce further actin depolymerization (FIG. 5G).

These findings explain previous observations of an unnecessary role of CXCR4 signaling in HIV-1 infection of transformed cell lines. For example, treatment of CXCR4 transfected U87-MG cells with P.T did not affect viral replication (B. J. Doranz et al., *J Virol* 73, 2752 (April, 1999)). Similarly, several CXCR4 mutants (2333b, 2442, 4442 and CXCR4-QAA) that were not capable of binding SDF-1 or mediating signaling still supported HIV replication in U87-MG cells (Doranz et al., (1999)). Thus, the requirement for cofilin activation is a unique feature only seen in resting T cells and not in transformed cell lines. It also was observed that stimulation of resting CD4 T cells with PHA plus IL-2 activated cofilin similarly to that of HIV-1 (FIG. 5H). These data confirmed that T cell activation can lead to cofilin activation rendering CXCR4 signaling unnecessary for HIV replication.

EXAMPLE 23

Cofilin Activation is Directly Involved in Viral Latent Infection

In resting CD4 T cells, cofilin is inhibited by phosphorylation at serine-3. The inhibition is maintained through the basal activity of the LIM family protein kinases for which ADF/cofilin proteins are the only known substrates (S. Arber et al., *Nature* 393, 805 (1998); N. Yang et al., *Nature* 393, 809 (1998)). To date, there is no known specific inhibitor for LIM kinases.

To demonstrate that activation of cofilin is directly involved in viral latent infection, a synthetic peptide was used to compete with cofilin for LIMK1 to inhibit cofilin phosphorylation. This peptide, S3, carries the N-terminal 16 residues including serine 3 of human cofilin. M. Nishita et al. *Molecular & Cellular Biology* 22, 774 (2002). To demonstrate competitive inhibition of cofilin phosphorylation by S3, an in vitro LIMK1 kinase assay was performed using a GST-tagged recombinant human cofilin-1 as the substrate.

Figure 6:
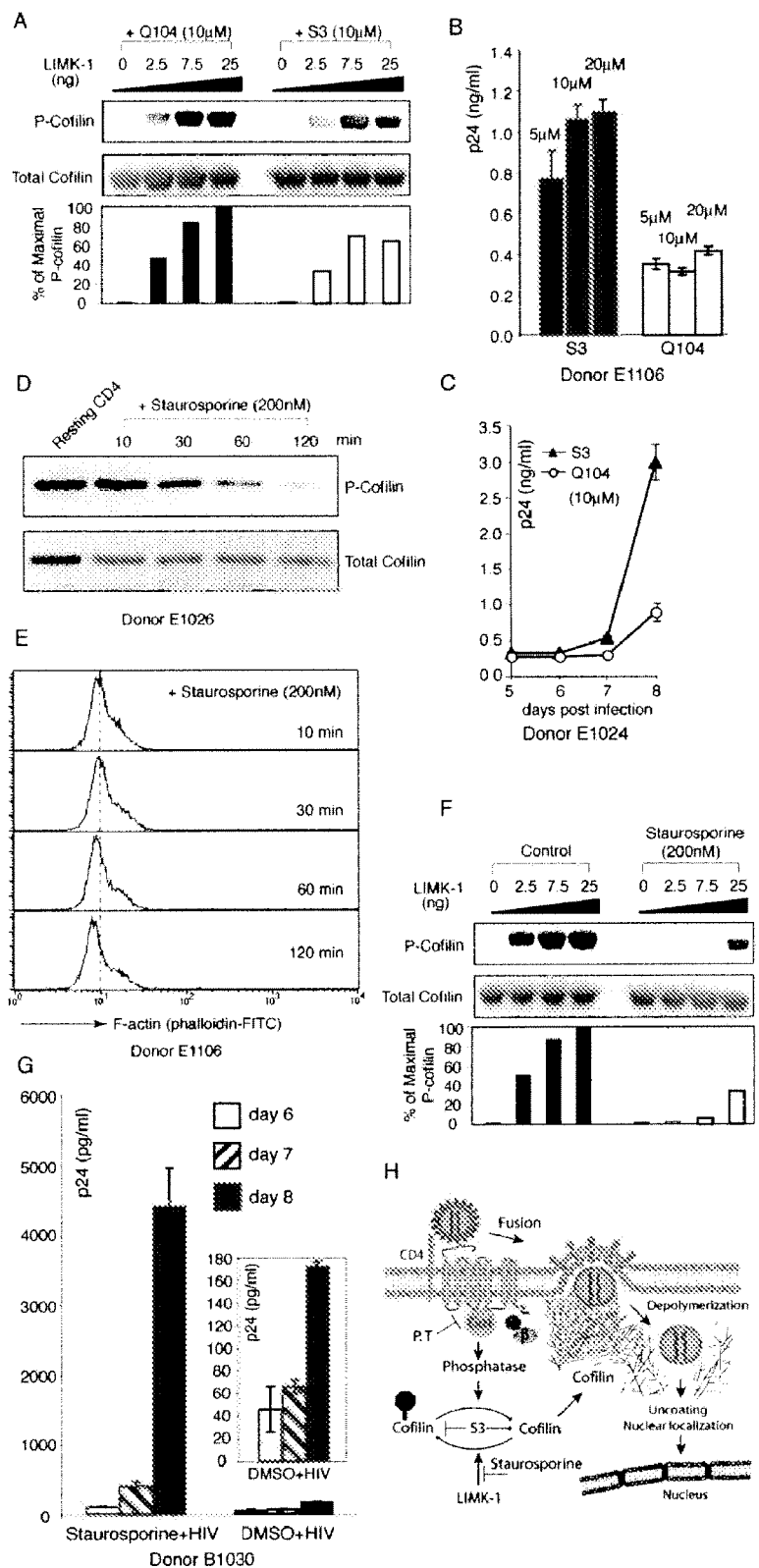
FIG. 6: Induction of active cofilin promotes vira latent infection of resting T cells.

FIG. 6 illustrates that induction of active cofilin promotes viral latent infection of resting T cells. FIG. 6A illustrates cofilin specific S3 peptide activates cofilin through competitive inhibition of cofilin phosphorylation by LIMK1. A recombinant human cofilin was used as the substrate in the in vitro LIMK1 kinase assay. Q104 was used as a control peptide. FIG. 6B illustrates dosage dependent enhancement of viral replication by S3. Cells were treated with S3 or Q104 for 2 hours, then infected, washed and cultured for 5 days and activated by anti-CD3/CD28 bead. Shown is p24 release at day 8. FIG. 6C shows viral replication course in cells similarly treated and infected as in FIG. 6B. FIG. 6D illustrates that staurosporine induces cofilin activation in resting T cells. Cells were treated with Staurosporine and immunoblotted for P-cofilin and total cofilin. FIG. 6E illustrates that staurosporine induces actin depolymerization in resting T cells. Staurosporine induces cofilin activation by direct inhibition of LIMK1, as shown in FIG. 6F. The in vitro LIMK1 kinase assay was performed as described above for FIG. 6A, in the presence or absence of Staurosporine. FIG. 6G shows enhancement of viral replication by Staurosporine. Resting cells were treated with Staurosporine for 2 hours, infected, washed and incubated for 5 days, then activated with anti-CD3/CD28 bead. FIG. 6H shows a model of gp120-CXCR4 signaling in mediating cofilin activation.

Because it was observed that S3 inhibited cofilin phosphorylation by LIMK1 (FIG. 6A), tests were performed to determine whether activation of cofilin by S3 would enhance viral replication. Resting CD4 T cells were pre-treated with S3 or a control peptide, Q104, then infected with HIV. S3 enhanced viral replication (FIG. 6, B and C) and this enhancement was consistently observed in multiple donors (data not shown). Thus, increasing cofilin activity directly enhances HIV-1 latent infection of resting CD4 T cells.

EXAMPLE 24

Kinase Inhibitors Affecting Cofilin Phosphorylation

Given the importance of cofilin for viral latent infection as demonstrated above, kinase inhibitors were screened for their ability to affect cofilin phosphorylation in resting T cells. Unexpectedly, it was discovered that staurosporine, a general serine/threonine kinase inhibitor (T. Tamaoki et al., *Biochem Biophys Res Commun* 135, 397 (1986), had a dramatic inhibition on cofilin phosphorylation. Brief treatment of resting CD4 T cells with 200 nM staurosporine led to gradual dephosphorylation and activation of cofilin in the absence of any stimulation (FIG. 6D). With the activation of cofilin, actin depolymerization also was observed in staurosporine treated cells (FIG. 6E). These results agree with data demonstrating that activation of cofilin leads to actin depolymerization in resting CD4 T cells (FIG. 5D).

To determine whether staurosporine acts on cofilin phosphorylation directly, the effect of staurosporine on the kinase activity of LIMKI in vitro using purified human cofilin-1 as the substrate was assayed as described above. At 200 nM, staurosporine directly inhibited the phosphorylation of cofilin by LIMK1 (FIG. 6F). This inhibition was much stronger than the competitive inhibition by the S3 peptide (FIG. 6A). Thus, staurosporine induces cofilin activation through direct inhibition on LIMK1. Based on these results, it was further tested whether staurosporine would facilitate viral replication. Remarkably, treatment of resting CD4 T cells with 200 nM staurosporine briefly before infection led to a dramatic enhancement in HIV replication (FIG. 6G). This enhancement was not due to enhancement on T cell activity by staurosporine.

Figure 9:
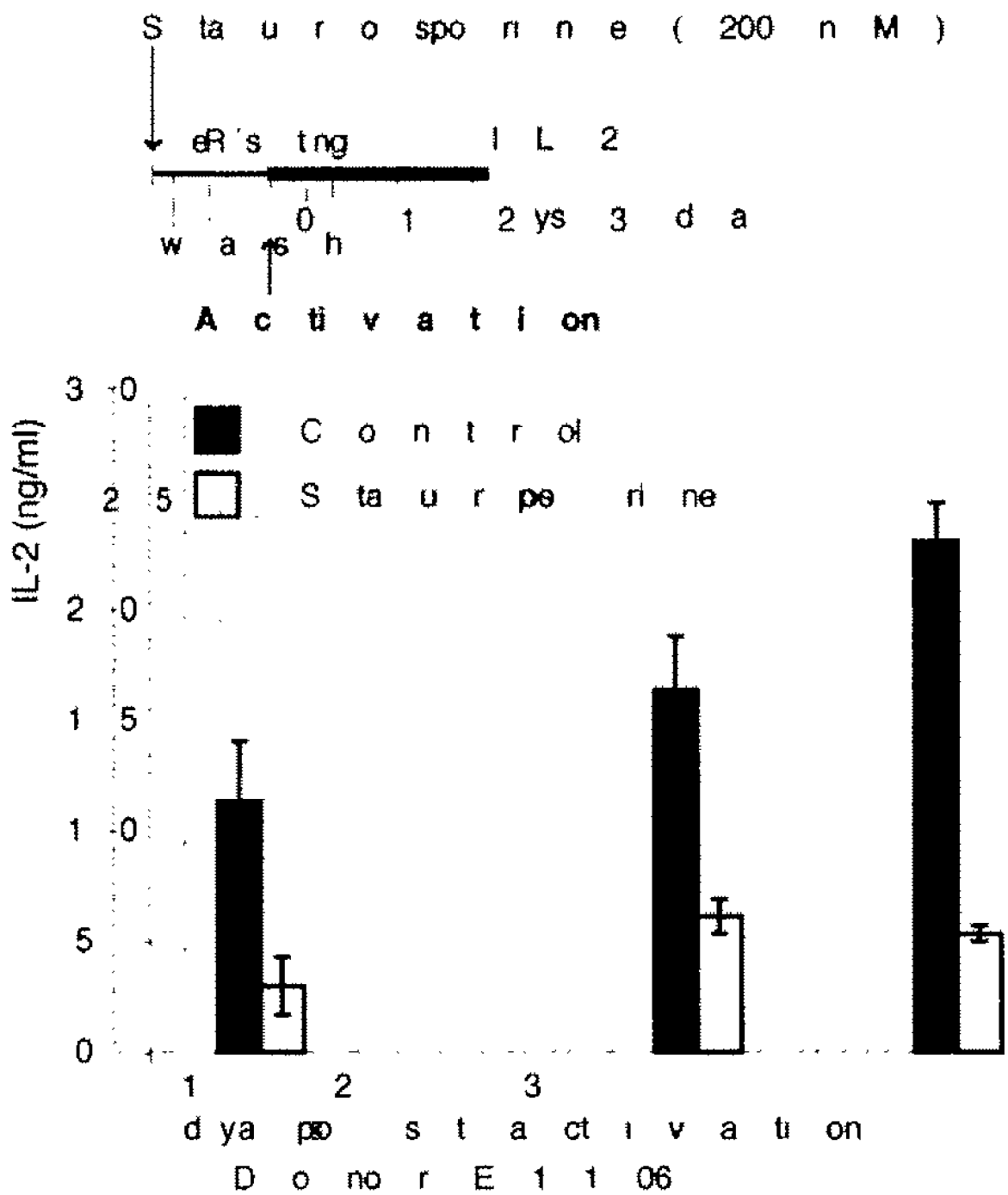
FIG. 9: Inhibition of IL-2 secretion by staurosporine.
Figure 10:
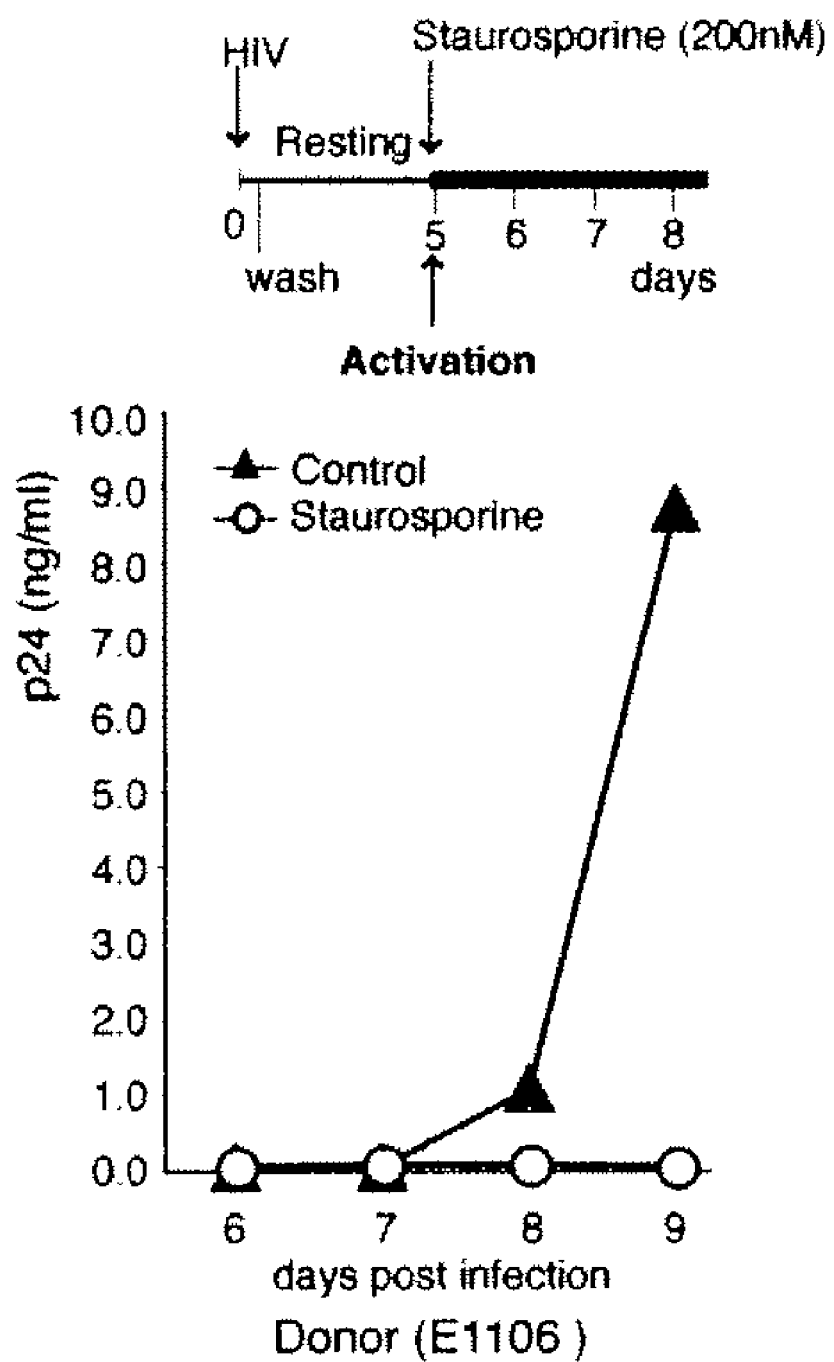
FIG. 10: Inhibition of T cell activation and viral replication by staurosporine.

When resting T cells were similarly treated with staurosporine, incubated and activated, there was a slight inhibition of IL-2 secretion by staurosporine (FIG. 9-10), consistent with previous demonstration of broad inhibitory effects of staurosporine on T cell activity. As shown in FIG. 10, resting CD4 T cells were infected with HIV-1, washed, then cultured for 5 days. At day 5, cells were activated by anti-CD3/CD28 bead (4 beads per cell) in the presence of 200 nM staurosporine. Viral p24 release was measured. Control cells were identically infected with HIV and activated in the absence of staurosporin.

Additionally, when staurosporine was added during T cell activation at day 5, it inhibited T cell activation and completely abolished HIV-1 replication.

Thus, given that staurosporine can cripple a large part of the signaling pathways critical for T cell activity while simultaneously activating cofilin and greatly enhancing viral replication, activation of cofilin is one of the most critical steps in HIV latent infection of resting T cells.

EXAMPLE 25

Cofilin Activation in HIV Positive Patients

Figure 11:
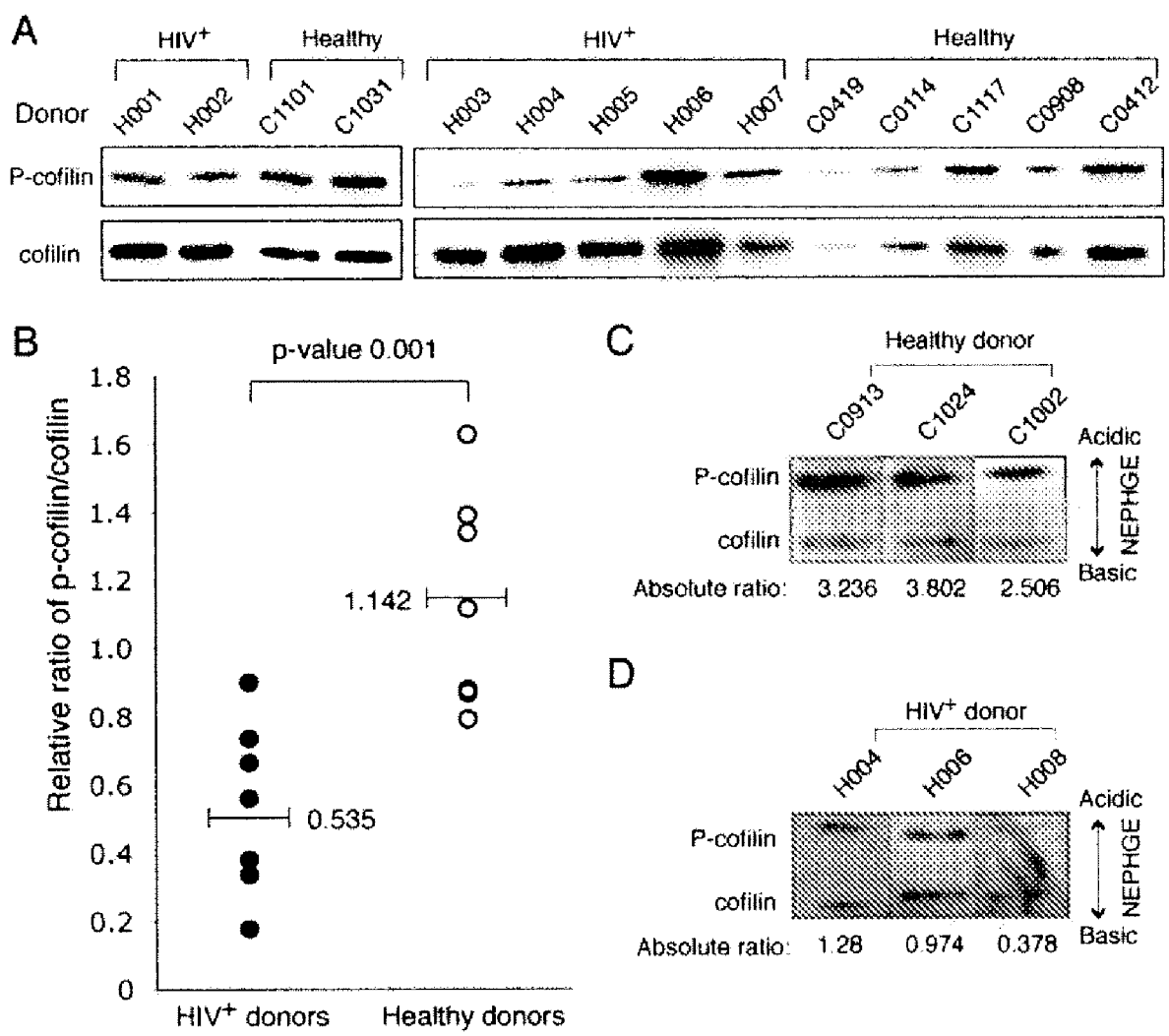
FIG. 11: Activation of Cofilin in HIV positive patients.
Figure 12:
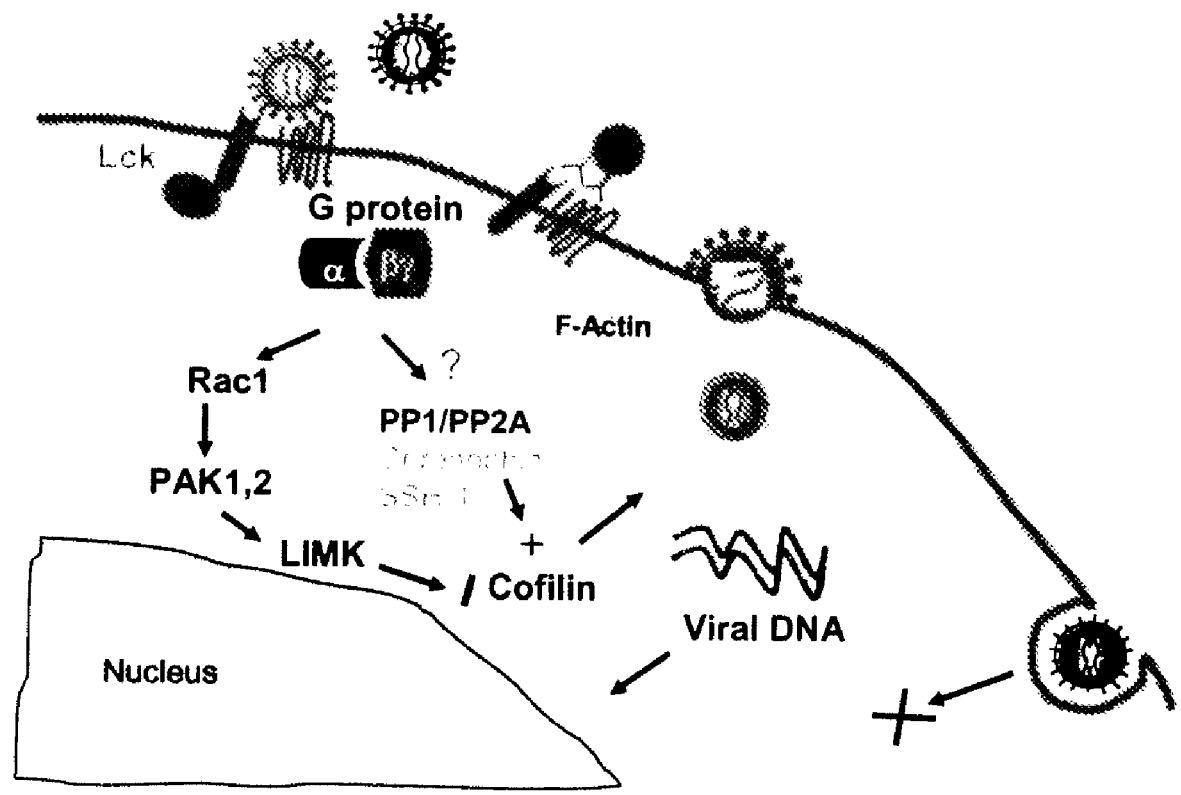
FIG. 12: Signaling Pathway for Cofilin Activation.

The phosphorylation state of cofilin in resting T-cells isolated from HIV patients was compared with that of healthy donors. As shown in FIG. 11, the ratio of active cofilin versus inactive cofilin shifts towards the dephosphorylated active form in resting T cells from HIV patients. This is the first report of cofilin dysregulation in a T-cell mediated immunodeficiency.

Resting CD4 T cells from five HIV patients on HAART therapy and five healthy donors were purified by negative depletion and then lysed and subsequently immunoblotted for P-cofilin (Ser3) or cofilin. (FIG. 11A). As illustrated in FIG. 11, activation of cofilin occurs in HIV positive patients. The relative ratio of P-cofilin to cofilin is plotted in FIG. 11B. HIV positive donors have statistically significant lower levels of P-cofilin/cofilin ($p=0.001$) suggesting higher levels of active cofilin. The results were confirmed by NEPHEGE western blotting using an anti-cofilin antibody. Shown are the absolute ratios of P-cofilin to active cofilin in three health donors (FIG. 11 C) and three HIV infected donors (FIG. 11D).

To control for slight differences in cell number the ratio of P-cofilin to cofilin in each donor was calculated by taking density measurements of the bands from the western blot using NIH imager software. In HIV patients, the ratio of P-cofilin to cofilin was significantly lower, with an average of 0.535 compared to 1.142 in healthy donors (p-value 0.001). These results suggest that in HIV patients there is a shift towards activated cofilin compared to healthy donors.

Large scale activation of cofilin in HIV patients is remarkable given the fact that a previous report found that there is only 0.2-16.4 HIV latently infected T cells per $10^6$ resting T cells in patients on HAART therapy. Despite this very minimal viral load, global cofilin activation in all the resting T cells purified from HIV patients on HAART therapy was observed. These finding suggest that cofilin activation could not occur simply as a result of direct HIV infection but is the result of indirect mechanisms perhaps through either viral or cellular gp120 shedding. In fact, it's been previously shown that gp120 treatment of resting CD4 T cells in vitro at concentrations below 50 nM result in cofilin dephosphorylation and subsequent activation.

The implications of cofilin activation in resting T cells in HIV patients are numerous. Currently, the only diagnostic markers for HIV disease progression are viral load numbers as calculated by PCR and total CD4 T cell count. It is widely accepted that there is a bystander effect of HIV-1 infected T cells on other non-infected cells, giving rise to apoptosis, anergy, and impaired T cell homing. However, there is no current way to quantify this T-cell change. The fact that cofilin plays a critical role in T cell activation, chemotaxis and, appears to be dysregulated in HIV patients, means cofilin activation could serve as a clinical marker of HIV disease progression.

EXAMPLE 26

Inhibition of HIV-1 Infection of Resting CD4 T Cells

Figure 13:
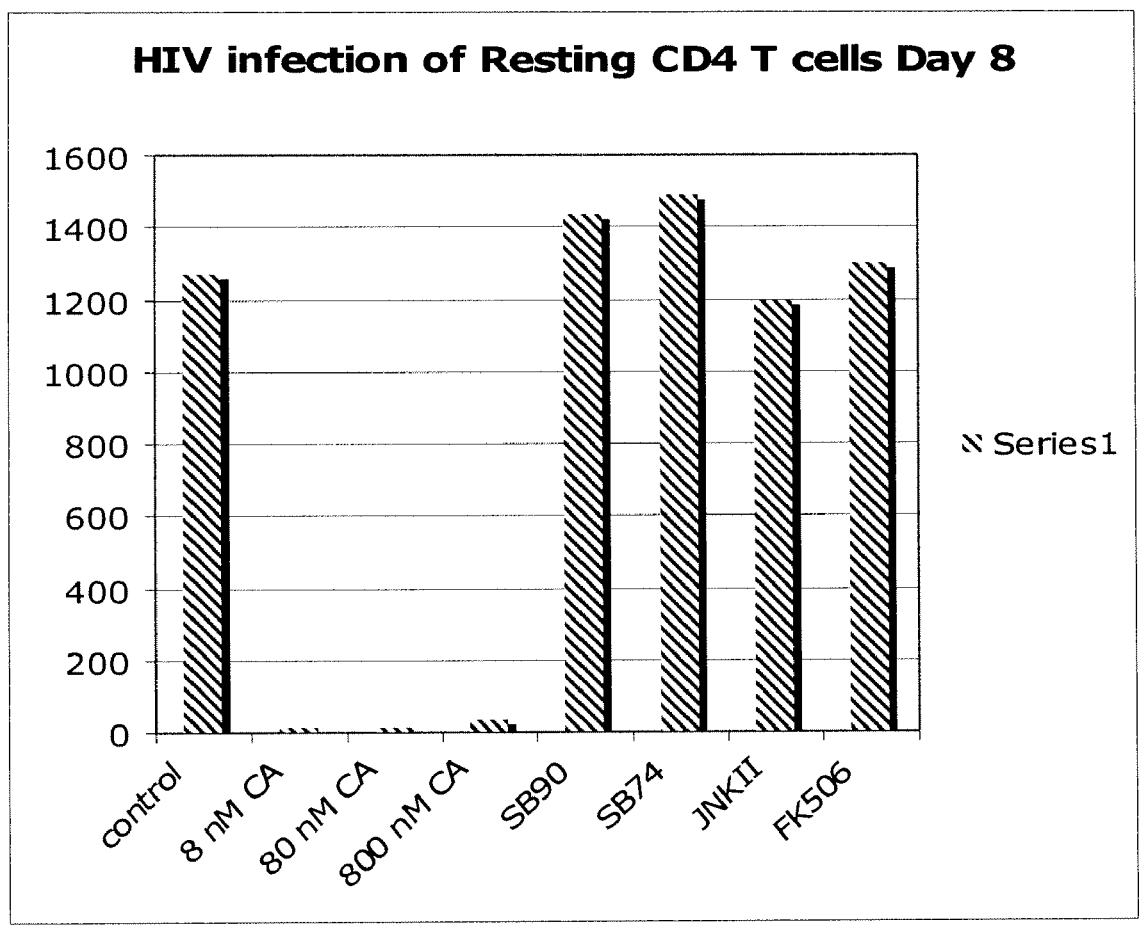
FIG. 13: Screening of HIV inhibitors. JNK inhibitor II inhibits C-Jun-N-terminal Kinase. CA stands for Calyculin A, an inhibitor for the phosphatase PP1a and PP2A. SB90 stands for SB 202190, an inhibitor for p38 Mapkinase. SB74 stands for SB 202474, a negative control for SB 90. FK 506 inhibits PP2B/Calcineurin. Control is cell infected with HIV with no drugs.
Figure 14:
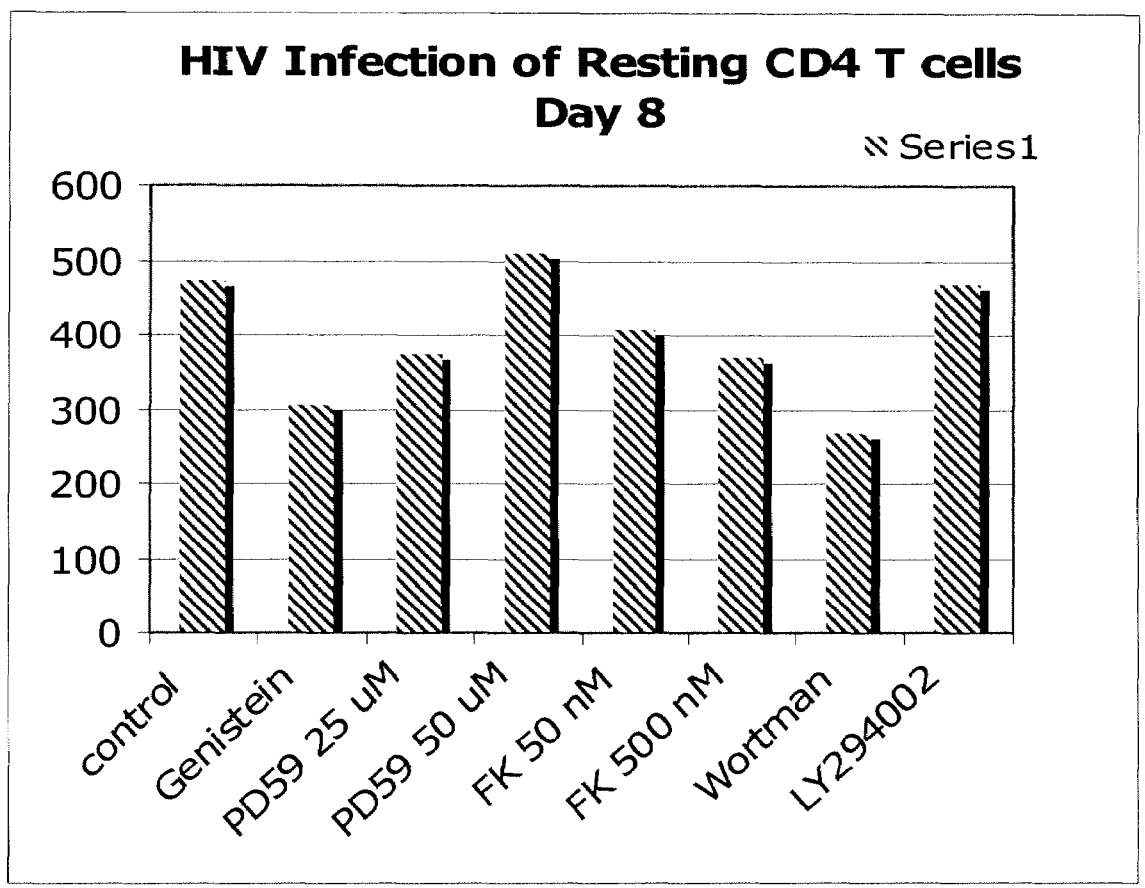
FIG. 14: Screening of HIV inhibitors. Genistein is a tyrosine kinase inhibitor. PD59 is a MAP kinase kinase inhibitor. FK506 is a calcineurin inhibitor. Wortmannin is a PI3K inhibitor. LY294002 is a PI3K inhibitor. Control is cell infected with HIV with no drugs.
Figure 15:
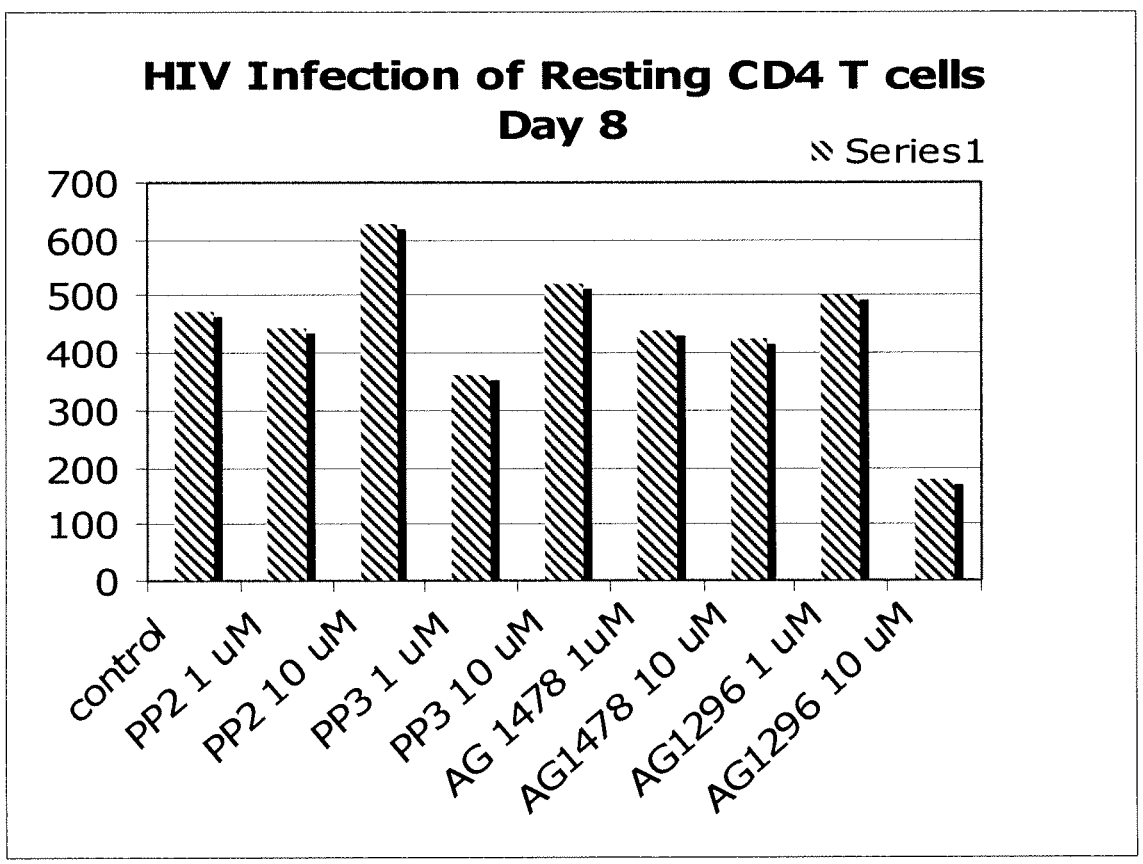
FIG. 15: Screening of HIV inhibitors. PP2 is a Src family tyrosine kinase inhibitor. PP3 is a negative control for PP2. AG1478 is a EGFR Kinase Inhibitor. AG1296 is a PDGF receptor kinase. Control is cell infected with HIV with no drugs.

We treated resting CD4 T cells with a variety of inhibitors for 2 hours before infection, then infected them with HIV-1 for 2 hours. After infection, cells were washed twice to remove the inhibitors and the cell-free virus. We incubated infected cells for 5 days, then activated the cells by adding anti-CD3/CD28 antibody coated magnetic beads (4 beads per cells). Then, we monitored viral replication daily from day 5 to 9. The results are depicted in FIGS. 13-15, which shows viral replication at day 8. The Y-axes show viral replication judged by release of viral p24 protein into the medium (pg/ml in p24 concentration).

TABLE 2

| SEQ ID NO: | Source | Sequence |
|---|---|---|
| 1 | Homo sapiens mRNA for cofilin, complete cds; GenBank gi: 219544 | atggcctccggtgtggctgtctctgatggtgtcatcaaggtgttc aacgacatgaaggtgcgtaagtcttcaacgccagaggaggtgaag aagcgcaagaaggcggtgctcttctgcctgagtgaggacaagaag aacatcatcctggaggagggcaaggagatcctggtgggcgatgtg ggccagactgtcgacgatccctacgccacctttgtcaagatgctg ccagataaggactgccgctatgccctctatgatgcaacctatgag accaaggagagcaagaaggaggatctggtgtttatcttctgggcc cccgagtctgcgccccttaagagcaaaatgatttatgccagctcc aaggacgccatcaagaagaagctgacagggatcaagcatgaattg caagcaaactgctacgaggaggtcaaggaccgctgcaccctggca gagaagctggggggcagtgcggtcatctccctggagggcaagcct tgtga |
| 2 | Homo sapiens cofilin protein sequence GenBank gi: 219545 | masgvavsdgvikvfndmkvrksstpeevkkrkkavlfclsedkk niileegkeilvgdvgqtvddpyatfvkmlpdkdcryalydatye tkeskkedlvfifwapesaplkskmiyasskdaikkkltgikhel qancyeevkdrctlaeklggsavislegkpl |

---

We claim:

1. A method for monitoring disease progression in a patient infected with HIV, comprising
    (A) measuring the phosphorylation level of cofilin in a sample from said patient, and
    (B) correlating a reduction in cofilin phosphorylation to a state below that normally present in resting T-cells to a progression of disease.

2. The method of claim 1, wherein the phosphorylation level is measured for the serine at amino acid position 3.

3. The method of claim 1, wherein said measuring is conducted by detecting a phosphorylation-driven conformational change on electron transport in a closed circuit comprising cofilin.

4. The method of claim 1, wherein the phosphorylation level is measured using an anti-phospho-cofilin (ser3) antibody.

5. The method of claim 2, wherein the phosphorylation level is measured using an anti-phospho-cofilin (ser3) antibody.

6. The method of claim 1, wherein said measurement comprises computing the ratio of phosphorylated cofilin to total cofilin and said correlation comprises correlating a ratio of less than one to a progression of disease.

* * * * *

SEQUENCE LISTING

<160> NUMBER OF SEQ ID NOS: 7

<210> SEQ ID NO 1
<211> LENGTH: 501
<212> TYPE: DNA
<213> ORGANISM: Homo sapiens

<400> SEQUENCE: 1

```
atggcctccg gtgtggctgt ctctgatggt gtcatcaagg tgttcaacga catgaaggtg      60
cgtaagtctt caacgccaga ggaggtgaag aagcgcaaga aggcggtgct cttctgcctg     120
agtgaggaca agaagaacat catcctggag gagggcaagg agatcctggt gggcgatgtg     180
ggccagactg tcgacgatcc ctacgccacc tttgtcaaga tgctgccaga taaggactgc     240
cgctatgccc tctatgatgc aacctatgag accaaggaga gcaagaagga ggatctggtg     300
tttatcttct gggcccccga gtctgcgccc cttaagagca aaatgattta tgccagctcc     360
aaggacgcca tcaagaagaa gctgacaggg atcaagcatg aattgcaagc aaactgctac     420
gaggaggtca aggaccgctg caccctggca gagaagctgg ggggcagtgc ggtcatctcc     480
ctggagggca agcctttgtg a                                               501
```

<210> SEQ ID NO 2
<211> LENGTH: 166
<212> TYPE: PRT
<213> ORGANISM: Homo sapiens

<400> SEQUENCE: 2

```
Met Ala Ser Gly Val Ala Val Ser Asp Gly Val Ile Lys Val Phe Asn
 1               5                  10                  15
```

-continued

```
Asp Met Lys Val Arg Lys Ser Ser Thr Pro Glu Glu Val Lys Lys Arg
         20                  25                  30
Lys Lys Ala Val Leu Phe Cys Leu Ser Glu Asp Lys Lys Asn Ile Ile
     35                  40                  45
Leu Glu Glu Gly Lys Glu Ile Leu Val Gly Asp Val Gly Gln Thr Val
 50                  55                  60
Asp Asp Pro Tyr Ala Thr Phe Val Lys Met Leu Pro Asp Lys Asp Cys
 65                  70                  75                  80
Arg Tyr Ala Leu Tyr Asp Ala Thr Tyr Glu Thr Lys Glu Ser Lys Lys
                 85                  90                  95
Glu Asp Leu Val Phe Ile Phe Trp Ala Pro Glu Ser Ala Pro Leu Lys
             100                 105                 110
Ser Lys Met Ile Tyr Ala Ser Ser Lys Asp Ala Ile Lys Lys Lys Leu
         115                 120                 125
Thr Gly Ile Lys His Glu Leu Gln Ala Asn Cys Tyr Glu Glu Val Lys
     130                 135                 140
Asp Arg Cys Thr Leu Ala Glu Lys Leu Gly Gly Ser Ala Val Ile Ser
145                 150                 155                 160
Leu Glu Gly Lys Pro Leu
                 165

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Met Ala Ser Gly Val Ala Val Ser Asp Gly Val Ile Lys Val Phe Asn
 1               5                  10                  15

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Trp Ala Pro Glu Ser Ala Pro Leu Gln Ser Gln Met
 1               5                  10

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gln Ile Lys Ile Trp Phe Gln Asn Arg Arg Met Lys Trp Lys Lys
 1               5                  10                  15

<210> SEQ ID NO 6
<211> LENGTH: 22
<212> TYPE: DNA
<213> ORGANISM: Artificial Sequence
<220> FEATURE:
```

-continued

```
<223> OTHER INFORMATION: Description of Artificial Sequence: Synthetic
      primer

<400> SEQUENCE: 6
ggttagacca gatctgagcc tg                                              22

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ttaataccga cgctctcgca cc                                              22
```